US011013815B2

(12) United States Patent
Nickerson-Nutter et al.

(10) Patent No.: US 11,013,815 B2
(45) Date of Patent: May 25, 2021

(54) HIGH-AFFINITY ANTI-HUMAN FOLATE RECEPTOR BETA ANTIBODIES AND METHODS OF USE

(71) Applicant: Monojul, LLC, Northbrook, IL (US)

(72) Inventors: Cheryl Nickerson-Nutter, Northbrook, IL (US); David Smolin, Northbrook, IL (US)

(73) Assignee: Monojul, LLC, Northbrook, IL (US)

( * ) Notice: Subject to any disclaimer, the term of this patent is extended or adjusted under 35 U.S.C. 154(b) by 0 days.

(21) Appl. No.: 16/008,878

(22) Filed: Jun. 14, 2018

(65) Prior Publication Data

US 2019/0117788 A1 Apr. 25, 2019

Related U.S. Application Data

(60) Provisional application No. 62/519,387, filed on Jun. 14, 2017.

(51) Int. Cl.

| | |
|---|---|
| ***A61K 47/68*** | (2017.01) |
| ***A61P 35/00*** | (2006.01) |
| ***C07K 16/28*** | (2006.01) |
| ***A61P 29/00*** | (2006.01) |
| ***A61K 39/00*** | (2006.01) |
| *A61K 47/69* | (2017.01) |
| *C07K 16/30* | (2006.01) |

(52) U.S. Cl.

CPC .......... *A61K 47/6817* (2017.08); *A61P 29/00* (2018.01); *A61P 35/00* (2018.01); *C07K 16/28* (2013.01); *A01K 2207/12* (2013.01); *A01K 2227/105* (2013.01); *A01K 2267/0331* (2013.01); *A61K 47/6849* (2017.08); *A61K 47/6911* (2017.08); *A61K 2039/505* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3061* (2013.01); *C07K 2317/565* (2013.01); *C07K 2317/73* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 8,871,206 | B2 * | 10/2014 | Low .................... | C07K 14/705 424/139.1 |
| 10,706,955 | B2 * | 7/2020 | Bremel ................. | G16B 20/00 |
| 2004/0258699 | A1 | 12/2004 | Bowdish et al. | |
| 2008/0260812 | A1 | 10/2008 | Matsuyama et al. | |
| 2013/0177570 | A1 | 7/2013 | Low et al. | |
| 2013/0287781 | A1 | 10/2013 | Clegg et al. | |
| 2014/0121123 | A1 | 5/2014 | Wang et al. | |

OTHER PUBLICATIONS

International Search Report and Written Opinion for International Application No. PCT/US2018/037584 dated Oct. 3, 2018.

Lynn et al. "High-affinity FRβ-specific CAR T cells eradicate AML and normal myeloid lineage without HSC toxicity," Leukemia, Feb. 22, 2016 (Feb. 22, 2016), vol. 30, pp. 1355-1364.

Feng et al. "A folate receptor beta-specific human monoclonal antibody recognizes activated macrophage of rheumatoid patients and mediates antibody dependent cell-mediated cytotoxicity," Arthritis Research & Therapy, Apr. 8, 2011 (Apr. 8, 2011), vol. 13, No. 2, pp. 1-12.

Lynn et al. "Targeting of Folate Receptor-Beta on Acute Myeloid Leukemia Blasts with Chimeric Antigen Receptor Expressing T Cells," Blood, Apr. 17, 2015 (Apr. 17, 2015), vol. 125, Iss. 22, pp. 3466-3476.

* cited by examiner

*Primary Examiner* — Padmavathi Baskar

(74) *Attorney, Agent, or Firm* — Husch Blackwell LLP

(57) ABSTRACT

Human anti-human folate receptor beta (FRβ) antibodies and antigen-binding fragments thereof are described, as well as methods of using such antibodies and fragments to treat a disorder, including but not limited to inflammatory disorders or cancers expressing cell surface FRβ.

20 Claims, 19 Drawing Sheets

Specification includes a Sequence Listing.

Folate Receptor Beta

MVWKWMPLLLLLVCVATMCSAQDRTDLLNVCMDAKHHKTKPGPEDKLHDQCSPWK
KNACCTASTSQELHKDTSRLYNFNWDHCGKMEPACKRHFIQDTCLYECSPNLGPWIQQ
VNQSWRKERFLDVPLCKEDCQRWWEDCHTSHTCKSNWHRGWDWTSGVNKCPAGAL
CRTFESYFPTPAALCEGLWSHSYKVSNYSRGSGRCIQMWFDSAQGNPNEEVARFYAAA
MHVNAGEMLHGTGGLLLSLALMLQLWLLG (SEQ ID NO. 22)

FIG. 1

EVQLVQSGAEVKKPGASVKVSCKASGYTFTSYAMHWVRQAPGQRLEWMGWINAGNGNTKYSQKFQGRVTITRDTSASTAYMELSSLRSEDTAVYYCARDISYGSFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTS (SEQ ID NO. 24)

FIG. 2A m909 heavy chain sequence

SSELTQDPAVSVALGQTVRITCQGDSLRSNYANWYQQKPGQAPVLVIYGQNNRPSGIPDRFSGSSSGNTASLTITGAQAADEADYYCDSRVSTGNHVVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS (SEQ ID NO. 25)

FIG. 2B m909 light chain sequence

ASO4498 Heavy Chain Sequence

EVQLVQSGAEVKKPGASVKVSCKASGYTFTYYAMHWVRQAPGQRLEWMGWINAGNGNTKYSQKFQGRVTITRDTSASTAYMELSSLRSEDTAVYYCARDISYGSFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPP (SEQ ID NO. 8)

FIG 3A

ASO4498 light chain sequence

MGWSWILLFLLSVTAGVHSSSELTQDPAVSVALGQTVRITCQGDSLRSNYANWYQQKPGQAPVLVIYGQFNRPSGIPDRFSGSSSGNTASLTITGAQAADEADYYCDSRVSTGIHVVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS (SEQ ID NO. 12)

FIG. 3B

AFFINITY MATURED AB #2 Heavy Chain Sequence

EVQLVQSGAEVKKPGASVKVSCKASGYTFTYYAMHWVRQAPGQRLEWMGWINAGNGNTKYSQKF
QGRVTITRDTSASTAYMELSSLRSEDTAVYYCARDISYGSFDYWGQGTLVTVSSASTKGPSVFP
LAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPP (SEQ ID NO. 8)

FIG. 4A

AFFINITY MATURED ANTIBODY #2 LIGHT CHAIN

SSELTQDPAVSVALGQTVRITCQGDSLRSNYANWYQQKPGQAPVLVIYGQNNRPSGIPDRFSGS
SSGNTASLTITGAQAADEADYYCDSRVSTGIHVVFGGGTKLTVLGQPKAAPSVTLFPPSSEELQ
ANKATLVCLISDFYPGAVTVAWKADSSPVKAGVETTTPSKQSNNKYAASSYLSLTPEQWKSHRS
YSCQVTHEGSTVEKTVAPTECS (SEQ ID NO. 16)

FIG. 4B

AFFINITY MATURED AB #3, HEAVY CHAIN SEQUENCE

EVQLVQSGAEVKKPGASVKVSCKASGYTFTYYAMHWVRQAPGQRLEWMGWINAGNG
FTKYSQKFQGRVTITRDTSASTAYMELSSLRSEDTAVYYCARDISYGSFDYWGQGTLVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPP (SEQ ID NO.18)

FIG. 5A

AFFINITY MATURED AB #3, LIGHT CHAIN SEQUENCE

SSELTQDPAVSVALGQTVRITCQGDSLRSNYANWYQQKPGQAPVLVIYGQFNLPSGIPD
RFSGSSSGNTASLTITGAQAADEADYYCDSRVSTGIHVVFGGGTKLTVLGQPKAAPSVT
LFPPSSEELQANKATLVCLISDFYPGAVTVAWKADSSPVKAGVETTTPSKQSNNKYAAS
SYLSLTPEQWKSHRSYSCQVTHEGSTVEKTVAPTECS (SEQ ID NO. 21)

HIGH-AFFINITY ANTI-HUMAN FOLATE RECEPTOR BETA ANTIBODIES AND METHODS OF USE

CROSS REFERENCE TO RELATED APPLICATIONS

This application is a non-provisional application of and claims priority to U.S. Provisional Patent Application No. 62/519,387 filed Jun. 14, 2017, which is incorporated herein by reference in its entirety.

FIELD

The disclosure relates to folate receptor beta (FRβ) binding agents, such as FRβ antibodies, and more particularly, to human monoclonal antibodies, or antigen-binding fragments thereof, that specifically bind human FRβ and methods of using FRβ binding agents.

SUBMISSION OF SEQUENCE LISTING

The contents of the electronic submission of the text file Sequence Listing, which is named MJL-39610-A.txt, which was created Jan. 8, 2019, and is 34.9 KB in size, is incorporated herein by reference in its entirety.

BACKGROUND

Folic acid is a vitamin required for the synthesis of nucleotide bases and is essential for the proliferation of all cells. Folates also are required for production of S-adenosylmethionine, the common substrate used in methylation of DNA, histones, G proteins, and many metabolic building blocks (see Kim, J Nutr 135:2703-2709 (2005); Loenen, Biochem Soc Trans 34:330-333 (2006)). Almost all cells take in folic acid via the reduced folate carrier or proton coupled folate transporter (see Matherly and Goldman, Vitam Horm 66:403-456 (2003)). Some cells, however, also express a folate receptor (FR) that binds folic acid about 100,000 times tighter than the aforementioned transporters, and carries bound folates into cells by receptor-mediated endocytosis (see Nakashima-Matsushita et al., Arth Rheum 42:1609-1616 (1999); Turk et al., Arthritis Rheumatoid 46:1947-1955 (2002)).

There are four members of the FR family: FRα, FRβ, FRγ and FR Δ (see Elnakat and Ratnam, Adv Drug Deliv Rev 56:1067-1084 (2004)). Different isoforms of the FR are used by certain cancer cells, activated macrophages, and the proximal tubule cells of the kidney to capture folates from their environment (see e.g., Nakashima-Matsushita et al. 1999, supra; and Turk et al. 2002, supra). A need exists for reagents and methods for differential targeting of the folate receptors for treatment of disease.

BRIEF SUMMARY

The disclosure provides binding agents, such as antibodies, that bind FRβ proteins, as well as compositions, such as pharmaceutical compositions, comprising the binding agents. In certain embodiments, the FRβ-binding agents are novel polypeptides, such as antibodies, antibody fragments, and other polypeptides related to such antibodies. In certain embodiments, the binding agents are antibodies that specifically bind human FRβ.

In one aspect, the disclosure provides a binding agent, such as an antibody, that specifically binds human FRβ. In some embodiments, the FRβ-binding agent or antibody modulates FRβ signaling, and/or inhibits FRβ signaling, and/or inhibits activation of FRβ. In some embodiments, the FRβ-binding agent inhibits FRβ signaling. In some embodiments, the FRβ-binding agent inhibits or interferes with binding of folate to FRβ.

In certain embodiments, the FRβ-binding agent is an antibody. In other embodiments, the antibody is a monoclonal antibody. In certain embodiments, the antibody is a humanized antibody. In certain embodiments, the antibody binds human FRβ. In certain embodiments, the FRβ-binding agent is the AS04498 antibody.

In certain embodiments, the antibody binds human FRβ with a $K_D$ of less than 10 nM. In certain embodiments, the antibody binds human FRβ with a $K_D$ of less than 5 nM. In one embodiment, the antibody binds human FRβ with a $K_D$ of less than 4 nM or with a $K_D$ of less than 2.5 nM. In one embodiment, the antibody binds human FRβ with a $K_D$ of less than 1 nM. In still another embodiment, the antibody binds human FRβ with a $K_D$ from 1 nM to 3 nM.

In one embodiment, the disclosure relates to methods of reducing the number of FRβ positive cells in a subject by administering a FRβ-binding agent, including but not limited to an antibody. In one embodiment, the disclosure relates to methods of reducing the number of activated macrophages expressing FRβ in a subject by administering a FRβ-binding agent, including but not limited to an antibody.

In one embodiment, the disclosure further provides methods of inhibiting the growth or survival of a cancer cell by administering the FRβ-binding agents to a subject with a cancer. The disclosure further provides methods of treating cancer by administering the FRβ-binding agents to a subject in need thereof. In some embodiments, the methods of treating cancer or inhibiting tumor growth comprise targeting cancer cells with the FRβ-binding agents. In certain embodiments, the methods comprise reducing the frequency of cancer cells in a tumor, reducing the number of cancer cells in a tumor, reducing the tumorigenicity of a tumor, and/or reducing the tumorigenicity of a tumor by reducing the number or frequency of cancer cells in the tumor.

In certain embodiments, the FRβ-binding agent is an antibody that comprises a heavy chain Complementary Determining Region 1 (CDR1) comprising GYTFTYYA (SEQ ID NO:1), a heavy chain Complementary Determining Region 2 (CDR2) comprising KYSQKFQ (SEQ ID NO:2), and a heavy chain Complementary Determining Region 3 (CDR3) comprising ARDISYGSFDYW (SEQ ID NO:3).

In some embodiments, the antibody further comprises a light chain CDR1 comprising SLRSNY (SEQ ID NO: 4), a light chain CDR2 comprising GQF (SEQ ID NO:5), and a light chain CDR3 comprising DSRVSTGIHVVF (SEQ ID NO:6).

In certain embodiments, the FRβ-binding agent is an antibody that comprises (a) a heavy chain CDR1 comprising GYTFTYYA (SEQ ID NO:1), or a variant thereof comprising 1, 2, 3, or 4 amino acid substitutions; (b) a heavy chain CDR2 comprising KYSQKFQ (SEQ ID NO:2), or a variant thereof comprising 1, 2, 3, or 4 amino acid substitutions and (c) a heavy chain CDR3 comprising ARDISYGSFDYW (SEQ ID NO:3), or a variant thereof comprising 1, 2, 3, or 4 amino acid substitutions.

In some embodiments, the FRβ-binding agent is an antibody that comprises (a) a light chain CDR1 comprising SLRSNY (SEQ ID NO:4), or a variant thereof comprising 1, 2, 3, or 4 amino acid substitutions; (b) a light chain CDR2 comprising GQF (SEQ ID NO:5), or a variant thereof comprising 1, or 2 amino acid substitutions and (c) a light chain CDR3 comprising DSRVSTGIHVVF (SEQ ID NO:6) or a variant thereof comprising 1, 2, 3, or 4 amino acid substitutions.

In certain embodiments, the FRβ-binding agent is an antibody that comprises (a) a heavy chain CDR1 comprising GYTFTYYA (SEQ ID NO:1), or a variant thereof comprising 1, 2, 3, or 4 amino acid substitutions; (b) a heavy chain CDR2 comprising KYSQKFQ (SEQ ID NO:2), or a variant thereof comprising 1, 2, 3, or 4 amino acid substitutions; (c) a heavy chain CDR3 comprising ARDISYGSFDYW (SEQ ID NO:3), or a variant thereof comprising 1, 2, 3, or 4 amino acid substitutions; (d) a light chain CDR1 comprising SLRSNY (SEQ ID NO:4), or a variant thereof comprising 1, 2, 3, or 4 amino acid substitutions; (e) a light chain CDR2 comprising GQF (SEQ ID NO:5), or a variant thereof comprising 1, or 2 amino acid substitutions; and (f) a light chain CDR3 comprising DSRVSTGIHVVF (SEQ ID NO:6) or a variant thereof comprising 1, 2, 3, or 4 amino acid substitutions. In some embodiments, the amino acid substitutions are conservative amino acid substitutions.

In certain embodiments, the FRβ-binding agent is an antibody that comprises: (a) a heavy chain variable region having at least 80% sequence identity to SEQ ID NO:7; and/or (b) a light chain variable region having at least 80% sequence identity to SEQ ID NO:11. In certain embodiments, the FRβ-binding agent is an antibody that comprises: (a) a heavy chain variable region having at least 90% sequence identity to SEQ ID NO:7; and/or (b) a light chain variable region having at least 90% sequence identity to SEQ ID NO:11.

In one embodiment, the FRβ-binding agent is an antibody that comprises a heavy chain region of SEQ ID NO: 8. In another embodiment, the FRβ-binding agent is an antibody that comprises a light chain region of SEQ ID NO: 12. In still another embodiment, the FRβ-binding agent is an antibody that comprises a heavy chain region of SEQ ID NO: 8 and a light chain region of SEQ ID NO: 12. In one embodiment, the FRβ-binding agent is AS04498 antibody.

In certain embodiments, the FRβ-binding agent is an antibody that comprises a heavy chain region having at least 80% sequence identity to SEQ ID NO: 8 or a heavy chain region having at least 90% sequence identity to SEQ ID NO: 8. In certain embodiments, the FRβ-binding agent is an antibody that comprises a heavy chain region having at least 80% sequence identity to SEQ ID NO: 9 or a heavy chain region having at least 90% sequence identity to SEQ ID NO: 9.

In certain embodiments, the FRβ-binding agent is an antibody that comprises a light chain region having at least 80% sequence identity to SEQ ID NO: 12 or a light chain region having at least 90% sequence identity to SEQ ID NO: 12.

In certain embodiments, the FRβ-binding agent is an antibody that comprises a heavy chain variable region of SEQ ID NO. 17. In another embodiment, the FRβ-binding agent is an antibody that comprises: (a) a heavy chain variable region having at least 80% sequence identity to SEQ ID NO:17; or a heavy chain variable region having at least 90% sequence identity to SEQ ID NO:17.

In certain embodiments, the FRβ-binding agent is an antibody that comprises a heavy chain region having at least 80% sequence identity to SEQ ID NO: 18 or a heavy chain region having at least 90% sequence identity to SEQ ID NO: 18. In certain embodiments, the FRβ-binding agent is an antibody that comprises a heavy chain region having at least 80% sequence identity to SEQ ID NO: 19 or a heavy chain region having at least 90% sequence identity to SEQ ID NO: 19.

In certain embodiments, the FRβ-binding agent is an antibody that comprises a light chain variable region of SEQ ID NO. 15. In another embodiment, the FRβ-binding agent is an antibody that comprises: (a) a light chain variable region having at least 80% sequence identity to SEQ ID NO:15; or a light chain variable region having at least 90% sequence identity to SEQ ID NO:15.

In certain embodiments, the FRβ-binding agent is an antibody that comprises a light chain region of SEQ ID NO. 16. In another embodiment, the FRβ-binding agent is an antibody that comprises a light chain region having at least 80% sequence identity to SEQ ID NO: 16 or a light chain region having at least 90% sequence identity to SEQ ID NO: 16.

In certain embodiments, the FRβ-binding agent is an antibody that comprises a light chain variable region of SEQ ID NO. 20. In another embodiment, the FRβ-binding agent is an antibody that comprises: (a) a light chain variable region having at least 80% sequence identity to SEQ ID NO:20; or a light chain variable region having at least 90% sequence identity to SEQ ID NO:20.

In certain embodiments, the FRβ-binding agent is an antibody that comprises a light chain region of SEQ ID NO. 21. In another embodiment, the FRβ-binding agent is an antibody that comprises a light chain region having at least 80% sequence identity to SEQ ID NO: 21 or a light chain region having at least 90% sequence identity to SEQ ID NO: 21.

In one embodiment, the disclosure relates to an antibody with a heavy chain having a sequence selected from the group consisting of: SEQ ID NO. 7, SEQ ID NO. 8, SEQ ID NO. 9, SEQ ID NO. 17, SEQ ID NO. 18, and SEQ ID NO. 19, and a light chain having a sequence selected from the group consisting of: SEQ ID NO. 11, SEQ ID NO. 12, SEQ ID NO. 15, SEQ ID NO. 16, SEQ ID NO. 20, and SEQ ID NO. 21.

In one embodiment, the disclosure relates to an antibody with a heavy chain having a sequence selected from the group consisting of: SEQ ID NO. 7, or a variant thereof comprising 1, 2, 3, or 4 amino acid substitutions, SEQ ID NO. 8, or a variant thereof comprising 1, 2, 3, or 4 amino acid substitutions, SEQ ID NO. 9, or a variant thereof comprising 1, 2, 3, or 4 amino acid substitutions, SEQ ID NO. 17, or a variant thereof comprising 1, 2, 3, or 4 amino acid substitutions, SEQ ID NO. 18, or a variant thereof comprising 1, 2, 3, or 4 amino acid substitutions and SEQ ID NO. 19, or a variant thereof comprising 1, 2, 3, or 4 amino acid substitutions and a light chain having a sequence selected from the group consisting of: SEQ ID NO. 11, or a variant thereof comprising 1, 2, 3, or 4 amino acid substitutions, SEQ ID NO. 12, or a variant thereof comprising 1, 2, 3, or 4 amino acid substitutions, SEQ ID NO. 15, or a variant thereof comprising 1, 2, 3, or 4 amino acid substitutions, SEQ ID NO. 16, or a variant thereof comprising 1, 2, 3, or 4 amino acid substitutions, SEQ ID NO. 20, or a variant thereof comprising 1, 2, 3, or 4 amino acid substitutions and SEQ ID NO. 21, or a variant thereof comprising 1, 2, 3, or 4 amino acid substitutions. In one embodiment, the variants referenced above can have one or more amino acid substations in the variable region, the framework region or both the variable region and the framework regions.

In another embodiment, the disclosure relates to a polypeptide selected from the group consisting of: SEQ ID NO. 7, SEQ ID NO. 8, SEQ ID NO. 9, SEQ ID NO. 11, SEQ ID NO. 12, SEQ ID NO. 15, SEQ ID NO. 16, SEQ ID NO. 17, SEQ ID NO. 18, SEQ ID NO. 19, SEQ ID NO. 20, and SEQ ID NO. 21.

In another embodiment, the disclosure relates to a composition comprising one or more polypeptides elected from the group consisting of: SEQ ID NO. 7, SEQ ID NO. 8, SEQ ID NO. 9, SEQ ID NO. 11, SEQ ID NO. 12, SEQ ID NO. 15, SEQ ID NO. 16, SEQ ID NO. 17, SEQ ID NO. 18, SEQ ID NO. 19, SEQ ID NO. 20, and SEQ ID NO. 21.

In one embodiment, the disclosure relates to an antibody or antibody fragment thereof having one or mutations in the $V_H$ region as shown in Table 4, with sequence location corresponding to FIG. 2A and SEQ ID NO. 24. In yet another embodiment, the disclosure relates to an antibody or antibody fragment thereof having one or mutations in the $V_L$ region as shown in Table 4, with sequence location corresponding to FIG. 2B and SEQ ID NO. 25.

In another embodiment, the disclosure relates to compositions including any of the FRβ-binding agents or antibodies described herein and a pharmaceutically acceptable carrier, and methods of using such compositions. For example, a composition can be used in a method of treating a patient having an inflammatory disorder (e.g., atherosclerosis, ischemia/reperfusion injury, transplantation rejection, vasculitis, inflammatory osteoarthritis, glomerulonephritis, restenosis, systemic sclerosis, fibromyalgia, sarcoidosis, or an autoimmune disease such as rheumatoid arthritis, systemic lupus erythematosus (SLE), ulcerative colitis, psoriasis, Type 1 diabetes, Crohn's disease, multiple sclerosis, and Sjogren's disease). The method can include administering to the patient an amount of a composition effective to reduce the number of FRβ positive macrophages and monocytes in the patient.

In another embodiment, the disclosure relates to a method of depleting activated macrophages from a human subject. The method includes administering to the subject a human monoclonal antibody, or antigen-binding fragment thereof, that specifically binds human FRβ, in an amount effective to reduce the number of activated macrophages in the subject.

In any of the methods described herein, the FRβ-binding agent or antibody can induce ADCC of FRβ expressing target cells.

In some embodiments, the antibody or fragment is defucosylated.

In any of the methods described herein, the FRβ-binding agent or antibody can induce opsonization-mediated clearance of FRβ expressing target cells.

In any of the methods described herein, the FRβ-binding agent or antibody can induce complement-mediated lysis of FRβ expressing target cells.

In other aspects, the disclosure provides methods of inhibiting growth of a cancer cell, comprising contacting the cell or a bodily fluid containing the cell with an effective amount of a FRβ-binding agent or antibody, including each of those described herein.

In another aspect, the disclosure provides a method of inhibiting the growth of a cancer cell in a subject, comprising administering to the subject a therapeutically effective amount of a FRβ-binding agent or antibody, including each of those described herein.

In another aspect, the disclosure provides a method of inhibiting folate receptor signaling in a cell, comprising contacting the cell with an effective amount of a FRβ-binding agent or antibody, including each of those described herein. In some embodiments, the cell is a tumor cell. In some embodiments, the tumor is a colorectal tumor. In some embodiments, the tumor is an ovarian tumor. In some embodiments, the tumor is a pancreatic tumor. In some embodiments, the tumor is a lung tumor. In some embodiments, the tumor expresses elevated levels of FRβ. In some embodiments, the tumor expresses elevated levels of FRβ. In certain embodiments, the FRβ-binding agent inhibits growth of the tumor, for example, by reducing the number and/or frequency of cancer stem cells in the tumor.

In another aspect, the disclosure provides methods of treating cancer in a subject. In some embodiments, the method comprises administering to a subject a therapeutically effective amount of any of the FRβ-binding agents or antibodies described above, as well as those described elsewhere herein. In some embodiments, the cancer is acute myeloid leukemia. In some embodiments, the cancer is pancreatic cancer. In some embodiments, the cancer is colorectal cancer. In some embodiments, the colorectal cancer comprises an inactivating mutation in the adenomatous polyposis coli (APC) gene. In some embodiments, the colorectal cancer does not comprise an inactivating mutation in the APC gene. In some embodiments, the colorectal cancer comprises a wild-type APC gene. In some embodiments, the cancer is ovarian cancer. In some embodiments, the cancer is breast cancer. In some embodiments, the cancer is lung cancer. In some embodiments, the cancer expresses elevated levels of FRβ protein. In some embodiments, the cancer is an ovarian cancer that expresses elevated levels of FRβ. In some embodiments, the cancer is colon cancer that expresses elevated levels of FRβ. In some embodiments, the cancer is a pancreatic cancer that expresses elevated levels of FRβ. In some embodiments, the cancer is a breast cancer that expresses elevated levels of FRβ. In some embodiments, the cancer is a lung cancer that expresses elevated levels of FRβ.

In another aspect, the disclosure provides methods of treating a disease in a subject wherein the disease is associated with FRβ expression, and/or aberrant FRβ signaling comprising administering a therapeutically effective amount of a FRβ-binding agent or antibody, including each of those described herein.

In certain embodiments of each of the aforementioned aspects, as well as other aspects and/or embodiments described elsewhere herein, the treatment methods comprise administering a FRβ-binding agent in combination with at least one additional therapeutic agent. In some embodiments, the treatment methods comprise administering a FRβ-binding agent in combination with a second FRβ-binding agent.

In certain embodiments of each of the aforementioned aspects, as well as other aspects and/or embodiments described elsewhere herein, the treatment methods further comprise a step of determining the level of FRβ protein expression in the tumor or cancer.

In another aspect, the disclosure provides a method of identifying a human subject or selecting a human subject for treatment with a FRβ-binding agent or antibody, including but not limited to, each of those described herein. In some embodiments, the method comprises determining if the subject has a tumor that has an elevated expression level of FRβ as compared to the expression of FRβ in normal tissue. In some embodiments, the method comprises identifying a subject for treatment or selecting a subject for treatment if the tumor has an elevated level of FRβ expression.

Pharmaceutical compositions comprising a FRβ-binding agent or antibody described herein and a pharmaceutically acceptable carrier are further provided, as are cell lines that produce the FRβ-binding agents. Methods of treating cancer and/or inhibiting tumor growth in a subject (e.g., a human)

comprising administering to the subject an effective amount of a composition comprising the FRβ-binding agents are also provided.

Where aspects or embodiments of the disclosure are described in terms of a Markush group or other grouping of alternatives, the disclosure encompasses not only the entire group listed as a whole, but also each member of the group individually and all possible subgroups of the main group, and also the main group absent one or more of the group members. The disclosure also envisages the explicit exclusion of one or more of any of the group members in the claimed embodiments.

BRIEF DESCRIPTION OF THE FIGURES

FIG. 1 is a depiction of the amino acid sequence of the full-length, unprocessed human FRβ protein (SEQ ID NO: 22). A fragment of the full-length protein containing residues 22 to 236 was used to produce recombinant FRβ.

FIG. 2A is a depiction of the amino acid sequence of the m909 Fab heavy chain sequence (SEQ ID NO: 24) and FIG. 2B is a depiction of the amino acid sequence of the m909 Fab light chain lambda sequence (SEQ ID NO: 25). Antibody m909 is a monoclonal antibody that binds human FRβ. In each of the sequences, the CDRs are underlined. By convention, numbering for framework regions 1-4 (FR1-FR4) is consecutive from the N-terminus, with FR1 being the most N-terminal sequence (not shown). By convention, numbering for Complementary Determining Regions (CDRs 1-3) is also consecutive from the N-terminus, with CDR1 being the most N-terminal (not shown).

FIG. 3A is a depiction of the amino acid sequence of the AS04498 Fab heavy chain sequence (SEQ ID NO: 8) and FIG. 3B is a depiction of the amino acid sequence of the AS04498 Fab light chain lambda sequence (SEQ ID NO: 12). In each of the sequences, the CDRs are underlined. By convention, numbering for framework regions 1-4 (FR1-FR4) is consecutive from the N-terminus, with FR1 being the most N-terminal sequence (not shown). By convention, numbering for Complementary Determining Regions (CDRs 1-3) is also consecutive from the N-terminus, with CDR1 being the most N-terminal (not shown).

FIG. 4A is a depiction of the amino acid sequence of the Fab heavy chain (SEQ ID NO: 8) of affinity matured antibody No. 2 binding to FRβ and FIG. 4B is a depiction of the amino acid sequence of the Fab light chain lambda sequence (SEQ ID NO: 16). In each of the sequences, the CDRs are underlined. By convention, numbering for framework regions 1-4 (FR1-FR4) is consecutive from the N-terminus, with FR1 being the most N-terminal sequence (not shown). By convention, numbering for Complementary Determining Regions (CDRs 1-3) is also consecutive from the N-terminus, with CDR1 being the most N-terminal (not shown).

FIG. 5A is a depiction of the amino acid sequence of the Fab heavy chain (SEQ ID NO: 18) of affinity matured antibody No. 3 binding to FRβ and FIG. 5B is a depiction of the amino acid sequence of the Fab light chain lambda sequence (SEQ ID NO: 21). In each of the sequences, the CDRs are underlined. By convention, numbering for framework regions 1-4 (FR1-FR4) is consecutive from the N-terminus, with FR1 being the most N-terminal sequence (not shown). By convention, numbering for Complementary Determining Regions (CDRs 1-3) is also consecutive from the N-terminus, with CDR1 being the most N-terminal (not shown).

DETAILED DESCRIPTION

I. Definitions

Figure 6A:
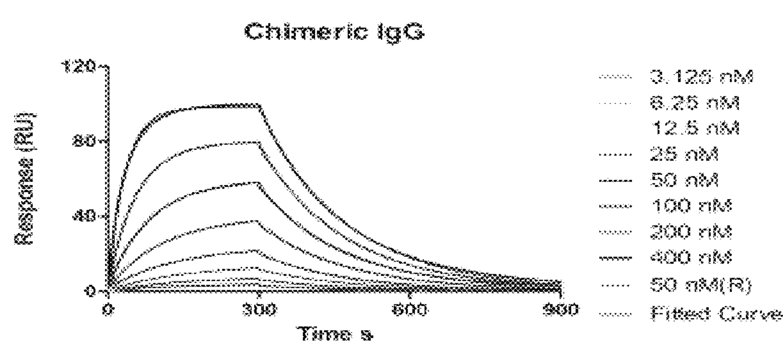
FIG. 6A is a line graph displaying the binding properties of chimeric IgG to FRβ at various concentrations of 3.125 nM, 6.25 nM, 12.5 nM, 25 nM, 50 nM, 100 nM, 200 nM, 400 nM.

To facilitate an understanding of the disclosure, a number of terms and phrases are defined below.

The terms "antagonist" and "antagonistic" as used herein refer to any molecule that partially or fully blocks, inhibits, reduces or neutralizes a biological activity of a target and/or signaling pathway (e.g., FRβ binding or FRβ signaling). The term "antagonist" is used herein to include any molecule that partially or fully blocks, inhibits, reduces or neutralizes the activity of a protein (e.g. FRβ protein). Suitable antagonist molecules specifically include, but are not limited to, antagonist antibodies or antibody fragments.

The terms "modulation" and "modulate" as used herein refer to a change or an alteration in a biological activity. Modulation includes, but is not limited to, stimulating or inhibiting an activity. Modulation may be an increase or a decrease in activity (e.g., a decrease in FRβ binding; a decrease in FRβ signaling), a change in binding characteristics, or any other change in the biological, functional, or immunological properties associated with the activity of a protein, pathway, or other biological point of interest.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) antibodies, multispecific antibodies such as bispecific antibodies generated from at least two intact antibodies, monospecific antibodies, monovalent antibodies, chimeric antibodies, humanized antibodies, human antibodies, fusion proteins comprising an antigen determination portion of an antibody, and any other modified immunoglobulin molecule comprising an antigen recognition site as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope binding site.

The term "variable region" of an antibody refers to the variable region of the antibody light chain, or the variable region of the antibody heavy chain, either alone or in combination. The variable regions of the heavy and light chain each consist of four framework regions (FR) connected by three complementarity determining regions (CDRs), also known as "hypervariable regions." The CDRs in each chain are held together in close proximity by the framework regions and, with the CDRs from the other chain, contribute to the formation of the antigen-binding sites of the antibody. There are at least two techniques for determining CDRs: (1) an approach based on cross-species sequence variability (i.e., Kabat et al., 1991, Sequences of Proteins of Immunological Interest, 5th Edition, National Institutes of Health, Bethesda Md.), and (2) an approach based on crystallographic studies of antigen-antibody complexes (Al-Lazikani et al., 1997, J. Mol. Biol., 273:927-948). In addition, combinations of these two approaches are sometimes used in the art to determine CDRs.

The term "monoclonal antibody" as used herein refers to a homogenous antibody population involved in the highly specific recognition and binding of a single antigenic determinant or epitope. This is in contrast to polyclonal antibodies that typically include a mixture of different antibodies directed against different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody portion, and any other modified immunoglobulin molecule comprising an antigen recognition site (antigen-binding site). Furthermore, "monoclonal antibody" refers to such antibodies made by any number of techniques, including but not limited to, hybridoma production, phage selection, recombinant expression, and transgenic animals.

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability (Jones et al., 1986, Nature, 321:522-525; Riechmann et al., 1988, Nature, 332:323-327; Verhoeyen et al., 1988, Science, 239:1534-1536).

In some instances, the Fv framework region residues of a human immunoglobulin are replaced with the corresponding residues in an antibody from a non-human species that has the desired specificity, affinity, and/or binding capability. The humanized antibody can be further modified by the substitution of additional residues either in the Fv framework region and/or within the replaced non-human residues to refine and optimize antibody specificity, affinity, and/or binding capability. In general, the humanized antibody will comprise substantially all of at least one, and typically two or three, variable domains containing all or substantially all of the CDRs that correspond to the non-human immunoglobulin whereas all or substantially all of the framework regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in, for example, U.S. Pat. No. 5,225,539.

The term "human antibody" as used herein refers to an antibody produced by a human or an antibody having an amino acid sequence corresponding to an antibody produced by a human made using any of the techniques known in the art. This definition of a human antibody specifically excludes a humanized antibody comprising non-human antigen-binding residues.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or binding capability, while the constant regions are homologous to the sequences in antibodies derived from another species (usually human) to avoid eliciting an immune response in that species.

The phrase "affinity matured antibody" as used herein refers to an antibody with one or more alterations in one or more CDRs thereof that result in an improvement in the affinity of the antibody for antigen, compared to a parent antibody that does not possess those alterations(s).

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

The terms "selectively binds" or "specifically binds" refers to a binding agent or an antibody that reacts or associates more frequently, more rapidly, with greater duration, with greater affinity, or with some combination of the above to the epitope, protein or target molecule than with alternative substances, including unrelated proteins. In certain embodiments "specifically binds" means, for instance, that an antibody binds a protein with a $K_D$ of about 0.1 mM or less, but more usually less than about 1 μM. In certain embodiments, "specifically binds" means that an antibody binds a target at times with a $K_D$ of at least about 0.1 μM or less, at other times at least about 0.01 μM or less, and at other times at least about 1 nM or less. Because of the sequence identity between homologous proteins in different species, specific binding can include an antibody that recognizes a protein in more than one species (e.g., human FRβ and mouse FRβ). Likewise, because of homology within certain regions of polypeptide sequences of different proteins, specific binding can include an antibody (or other polypeptide or binding agent) that recognizes more than one protein. It is understood that, in certain embodiments, an antibody or binding moiety that specifically binds a first target may or may not specifically bind a second target. As such, "specific binding" does not necessarily require (although it can include) exclusive binding, i.e. binding to a single target. Thus, an antibody may, in certain embodiments, specifically bind more than one target. In certain embodiments, multiple targets may be bound by the same antigen-binding site on the antibody. For example, an antibody may, in certain instances, comprise two identical antigen-binding sites, each of which specifically binds the same epitope on two or more proteins. In certain alternative embodiments, an antibody may be bispecific or multispecific and comprise at least two antigen-binding sites with differing specificities. By way of non-limiting example, a bispecific antibody may comprise one antigen-binding site that recognizes an epitope on one protein (e.g., human FRβ) and further comprise a second, different antigen-binding site that recognizes a different epitope on a second protein. Generally, but not necessarily, reference to binding means specific binding The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies, in certain embodiments, the polypeptides can occur as single chains or associated chains.

The terms "polynucleotide" and "nucleic acid" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

"Conditions of high stringency" may be identified by those that: (1) employ low ionic strength and high temperature for washing, for example 15 mM sodium chloride/1.5 mM sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75M NaCl, 75 mM sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 50% formamide at 55° C., followed by a high-stringency wash consisting of 0.1×SSC containing EDTA at 55° C.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies disclosed herein do not abrogate the binding of the polypeptide or antibody containing the amino acid sequence, to the antigen(s), i.e., FRβ to which the polypeptide or antibody binds. Methods of identifying nucleotide and amino acid conservative substitutions which do not eliminate antigen binding are well-known in the art.

The term "vector" as used herein refers to a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some embodiments, a polypeptide, antibody, polynucleotide, vector, cell, or composition which is isolated is substantially pure.

The term "substantially pure" as used herein refers to material that is at least 50% pure (i.e., free from contaminants), at least 90% pure, at least 95% pure, at least 98% pure, or at least 99% pure.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma, leukemia and acute myeloid leukemia.

The terms "tumor" and "neoplasm" as used herein refer to any mass of tissue that results from excessive cell growth or proliferation, either benign (noncancerous) or malignant (cancerous) including pre-cancerous lesions.

The term "metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell" and "CSC" and "tumor stem cell" and "tumor initiating cell" are used interchangeably herein and refer to cells from a cancer or tumor that: (1) have extensive proliferative capacity; (2) are capable of asymmetric cell division to generate one or more types of differentiated cell progeny wherein the differentiated cells have reduced proliferative or developmental potential; and (3) are capable of symmetric cell divisions for self-renewal or self-maintenance. These properties confer on the cancer stem cells the ability to form or establish a tumor or cancer upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein refers to the ability of a random sample of cells from the tumor to form palpable tumors upon serial transplantation into immunocompromised hosts (e.g., mice).

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to approved or approvable by a regulatory agency of the Federal or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one binding agent (e.g., an antibody) of the present disclosure, and which does not destroy the pharmacological activity thereof and is nontoxic when administered in doses sufficient to deliver a therapeutic effect.

The terms "effective amount" or "therapeutically effective amount" or "therapeutic effect" refer to an amount of a binding agent, an antibody, polypeptide, polynucleotide, small organic molecule, or other drug effective to "treat" a disease or disorder in a subject or mammal. In the case of cancer, the therapeutically effective amount of a drug (e.g., an antibody) has a therapeutic effect and as such can reduce the number of cancer cells; decrease tumorigenicity, tumorigenic frequency or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects. To the extent the agent, for example an antibody, prevents growth and/or kills existing cancer cells, it can be referred to as cytostatic and/or cytotoxic.

The terms "treating" or "treatment" or "to treat" or "alleviating" or "to alleviate" refer to: (1) therapeutic measures that cure, slow down, lessen symptoms of, and/or halt progression of a diagnosed pathologic condition or disorder and/or (2) prophylactic or preventative measures that prevent or slow the development of a targeted pathologic condition or disorder. Thus, those in need of treatment include those already with the disorder; those prone to have the disorder; and those in whom the disorder is to be prevented.

In some embodiments, a subject is successfully "treated" according to the methods disclosed herein if the patient shows one or more of the following: a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a," "an," and "the" include plural forms unless the context clearly dictates otherwise.

It is understood that wherever embodiments are described herein with the language "comprising" otherwise analogous embodiments described in terms of "consisting of" and/or "consisting essentially of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. FRβ

In one embodiment, the disclosure provides a FRβ-binding agent or antibody as well as methods of using such FRβ-binding agent or antibody to treat, detect, or monitor a cell expressing FRβ in a subject (e.g., a human patient). In one embodiment, the cell is a macrophage. In yet another, the cell is an activated macrophage.

In one embodiment, the disclosure provides a FRβ-binding agent or antibody as well as methods of using such FRβ-binding agent or antibody to treat, detect, or monitor an inflammatory disorder or a cancer expressing FRβ in a subject (e.g., a human patient). The term "FRβ" as used herein refers to human folate receptor beta. The amino acid sequence of human FRβ can be found in FIG. 1 (SEQ ID NO: 22) and in GenBank under Accession No. NP_001107007. FRβ is a differential marker on the surface of myelomonocytic lineage cells. In normal tissues, FRβ is expressed in placenta, myelomonocytic lineage cells (e.g., monocytes and macrophages), and mature neutrophils. FRβ, however, does not bind folic acid on quiescent macrophages until the myeloid cell becomes activated. FRβ is consistently detected in multiple myeloma cells, chronic myeloid leukemia (CML) cells, and in 70% of acute myeloid leukemia (AML) cells. FRβ also has been detected by RT-PCR in solid tumors (e.g., carcinomas from colon, kidney, breast, ovary, uterus, or lung; squamous cell carcinomas of the head and neck; and malignancies of non-epithelial origin such as sarcomas, lymphomas, fibrous histiocytomas, ovarian granulosa cell tumor, astrocytoma, meningiomas, and Wilms' tumor). See, for example, Ross et al., Cancer, 73:2432-43 (1994).

In monocytes and macrophage-lineage cells, FRβ expression is increased upon activation. For example, FRβ is expressed and functional in synovial macrophages in rheumatoid arthritis patients. Furthermore, γ-scintigraphy images of patients with a variety of inflammatory disorders (e.g., rheumatoid arthritis, Crohn's disease, ischemic bowel disease, Sjogren's syndrome, localized infections, atherosclerosis, and organ transplant rejection) show uptake of a folate-targeted $^{99m}$Tc imaging agent (EC20) at sites of inflammation (see Low et al., Acc Chem Res. 41(1):120-9 (2008); Matteson et al., Clin Exp Rheumatol 27:253-259 (2009); and Ayala-Lopez et al., J Nuc Med, 51:768-774 (2010)). These findings indicate expression of FRβ in activated macrophages and monocytes.

The FRβ-binding agent or antibodies described herein specifically bind FRβ, and do not detectably bind FRα. In some embodiments, the FRβ-binding agents or antibodies described herein also do not detectably bind FRγ and/or FR-delta. FRα is expressed on the apical surfaces of a few epithelial cell types (primarily proximal tubules of the kidneys and alveolar epithelial cells of the lungs) and is upregulated on a variety of epithelial-derived tumors. FRγ is rarely expressed and difficult to detect in vivo. FR-delta is expressed on regulatory T cells, where it exhibits only very low affinity for folic acid. As such, the FRβ-binding agents or antibodies, which specifically bind FRβ, can be used for depleting activated macrophages, treating inflammatory disorders, and treating cancers that express FRβ.

III. FRβ-Binding Agents

The disclosure provides agents that bind human FRβ protein. These agents are referred to herein as "FRβ-binding agents." In some embodiments, the FRβ-binding agents are antibodies. In some embodiments, the FRβ-binding agents are polypeptides. In certain embodiments, the FRβ-binding agents bind FRβ.

In one embodiment, the FRβ-binding agent is a fully human, monoclonal antibody. In certain embodiments, the FRβ-binding agent is an antibody that comprises a heavy chain CDR1 comprising GYTFTYYA (SEQ ID NO: 1), or a variant thereof comprising 1, 2, 3, or 4 amino acid substitutions. In another embodiment, the FRβ-binding agent is an antibody that comprises a heavy chain CDR2 comprising KYSQKFQ (SEQ ID NO: 2), or a variant thereof comprising 1, 2, 3, or 4 amino acid substitutions. In yet another embodiment, the FRβ-binding agent is an antibody that comprises a heavy chain CDR3 comprising ARDISYGSFDYW (SEQ ID NO: 3), or a variant thereof comprising 1, 2, 3, or 4 amino acid substitutions.

In certain embodiments, the FRβ-binding agent is an antibody that comprises a heavy chain CDR1 comprising GYTFTYYA (SEQ ID NO: 1), a heavy chain CDR2 comprising KYSQKFQ (SEQ ID NO:2), and a heavy chain CDR3 comprising ARDISYGSFDYW (SEQ ID NO: 3).

In certain embodiments, the FRβ-binding agent is an antibody that comprises: (a) a heavy chain CDR1 comprising GYTFTYYA (SEQ ID NO: 1), or a variant thereof comprising 1, 2, 3, or 4 amino acid substitutions; (b) a heavy chain CDR2 comprising KYSQKFQ (SEQ ID NO: 2), or a variant thereof comprising 1, 2, 3, or 4 amino acid substitutions and (c) a heavy chain CDR3 comprising ARDISYGSFDYW (SEQ ID NO: 3), or a variant thereof comprising 1, 2, 3, or 4 amino acid substitutions.

In some embodiments, the FRβ-binding agent is an antibody that comprises a light chain CDR1 comprising SLRSNY (SEQ ID NO: 4), or a variant thereof comprising 1, 2, 3, or 4 amino acid substitutions. In some embodiments, the FRβ-binding agent is an antibody that comprises a light chain CDR2 comprising GQF (SEQ ID NO: 5), or a variant thereof comprising 1, or 2 amino acid substitutions. In some embodiments, the FRβ-binding agent is an antibody that comprises a light chain CDR3 comprising DSRVSTGIHVVF (SEQ ID NO: 6) or a variant thereof comprising 1, 2, 3, or 4 amino acid substitutions.

In some embodiments, the FRβ-binding agent is an antibody that comprises a light chain CDR1 comprising SLRSNY (SEQ ID NO: 4), or a variant thereof comprising 1, 2, 3, or 4 amino acid substitutions; (b) a light chain CDR2 comprising GQF (SEQ ID NO: 5), or a variant thereof comprising 1, or 2 amino acid substitutions; and (c) a light chain CDR3 comprising DSRVSTGIHVVF (SEQ ID NO: 6) or a variant thereof comprising 1, 2, 3, or 4 amino acid substitutions.

In certain embodiments, the FRβ-binding agent is an antibody which comprises: an antibody that comprises (a) a heavy chain CDR1 comprising GYTFTYYA (SEQ ID NO: 1), or a variant thereof comprising 1, 2, 3, or 4 amino acid substitutions; (b) a heavy chain CDR2 comprising KYSQKFQ (SEQ ID NO: 2), or a variant thereof comprising 1, 2, 3, or 4 amino acid substitutions; (c) a heavy chain CDR3 comprising ARDISYGSFDYW (SEQ ID NO: 3), or a variant thereof comprising 1, 2, 3, or 4 amino acid substitutions; (d) a light chain CDR1 comprising SLRSNY (SEQ ID NO: 4), or a variant thereof comprising 1, 2, 3, or 4 amino acid substitutions; (e) a light chain CDR2 comprising GQF (SEQ ID NO: 5), or a variant thereof comprising 1, or 2 amino acid substitutions; and (f) a light chain CDR3 comprising DSRVSTGIHVVF (SEQ ID NO: 6) or a variant thereof comprising 1, 2, 3, or 4 amino acid substitutions. In some embodiments, the amino acid substitutions are conservative amino acid substitutions.

In some embodiments, the antibody or antigen binding fragment thereof comprises the heavy chain variable region ($V_H$) amino acid sequence set forth in SEQ ID NO: 7: EVQLVQSGAEVKKPGASVKVSCKASGYTFTYYAMHWVRQAPGQRLEWMGWI NAGNGNTKYSQKFQGRVTITRDTSASTAYMELSSLRSEDTAVYYCARDISYGSF DYWGQGTLVTVSS. Alternatively, or in addition, the antibody or antigen binding fragment thereof comprises the light chain variable region amino ($V_1$) amino acid sequence set forth in SEQ ID NO: 11:

```
SSELTQDPAVSVALGQTVRITCQGDSLRSNYANWYQQKPGQAPVLVIYGQ
FNRPSGIPDRFSGSSSGNTASLTITGAQAADEADYYCDSRVSTGIHVVFG
GGTKLTVLG.
```

In some embodiments, an antibody or fragment thereof comprising such sequences is designated AS04498 and specifically binds to human FRβ. In one embodiment, AS04498 has a s heavy chain amino acid sequence as set forth in SEQ ID NO. 8 and a light chain amino acid sequence as set forth in SEQ ID NO. 12.

In some embodiments, the antibody or antigen binding fragment thereof comprises a heavy chain amino acid sequence set forth in SEQ ID NO: 8:

```
EVQLVQSGAEVKKPGASVKVSCKASGYTFTYYAMHWVRQAPGQRLEWMGW
INAGNGNTKYSQKFQGRVTITRDTSASTAYMELSSLRSEDTAVYYCARDI
```

-continued

```
SYGSFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTH.
```

In some embodiments, the antibody or antigen binding fragment thereof comprises a heavy chain amino acid sequence set forth in SEQ ID NO: 9:

```
MGWSWILLFLLSVTAGVHSEVQLVQSGAEVKKPGASVKVSCKASGYTFTY
YAMHWVRQAPGQRLEWMGWINAGNGNTKYSQKFQGRVTITRDTSASTAYM
ELSSLRSEDTAVYYCARDISYGSFDYWGQGTLVTVSSASTKGPSVFPLAP
SSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHE
ALHNHYTQKSLSLSPGK
```

In some embodiments, the antibody or antigen binding fragment thereof comprises a light chain amino acid sequence set forth in SEQ ID NO: 12:

```
MGWSWILLFLLSVTAGVHSSSELTQDPAVSVALGQTVRITCQGDSLRSNY
ANWYQQKPGQAPVLVIYGQFNRPSGIPDRFSGSSSGNTASLTITGAQAAD
EADYYCDSRVSTGIHVVFGGGTKLTVLGQPKAAPSVTLFPPSSEELQANK
ATLVCLISDFYPGAVTVAWKADSSPVKAGVETTTPSKQSNNKYAASSYLS
LTPEQWKSHRSYSCQVTHEGSTVEKTVAPTECS.
```

In some embodiments, the antibody or antigen binding fragment thereof comprises the light chain variable region amino ($V_1$) amino acid sequence set forth in SEQ ID NO:15:

```
SSELTQDPAVSVALGQTVRITCQGDSLRSNYANWYQQKPGQAPVLVIYGQ
NNRPSGIPDRFSGSSSGNTASLTITGAQAADEADYYCDSRVSTGIHVVFG
GGTKLTVLG
```

In some embodiments, the antibody or antigen binding fragment thereof comprises a light chain amino acid sequence set forth in SEQ ID NO: 16:

```
MGWSWILLFLLSVTAGVHSSSELTQDPAVSVALGQTVRITCQGDSLRSNY
ANWYQQKPGQAPVLVIYGQNNRPSGIPDRFSGSSSGNTASLTITGAQAAD
EADYYCDSRVSTGIHVVFGGGTKLTVLGQPKAAPSVTLFPPSSEELQANK
ATLVCLISDFYPGAVTVAWKADSSPVKAGVETTTPSKQSNNKYAASSYLS
LTPEQWKSHRSYSCQVTHEGSTVEKTVAPTECS.
```

In some embodiments, the antibody or antigen binding fragment thereof comprises the heavy chain variable region ($V_H$) amino acid sequence set forth in SEQ ID NO:17:

EVQLVQSGAEVKKPGASVKVSCKASGYTFTYYAMHWVRQAPGQRLEWMGW
INAGNGFTKYSQKFQGRVTITRDTSASTAYMELSSLRSEDTAVYYCARDI
SYGSFDYWGQGTLVTVSS.

In some embodiments, the antibody or antigen binding fragment thereof comprises a heavy chain amino acid sequence set forth in SEQ ID NO 18:

EVQLVQSGAEVKKPGASVKVSCKASGYTFTYYAMHWVRQAPGQRLEWMGW
INAGNGFTKYSQKFQGRVTITRDTSASTAYMELSSLRSEDTAVYYCARDI
SYGSFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTH

In some embodiments, the antibody or antigen binding fragment thereof comprises a heavy chain amino acid sequence set forth in SEQ ID NO 19:

MGWSWILLFLLSVTAGVHSEVQLVQSGAEVKKPGASVKVSCKASGYTFTY
YAMHWVRQAPGQRLEWMGWINAGNGFTKYSQKFQGRVTITRDTSASTAYM
ELSSLRSEDTAVYYCARDISYGSFDYWGQGTLVTVSSASTKGPSVFPLAP
SSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHE
ALHNHYTQKSLSLSPGK

In some embodiments, the antibody or antigen binding fragment thereof comprises the light chain variable region amino ($V_1$) amino acid sequence set forth in SEQ ID NO: 20:

SSELTQDPAVSVALGQTVRITCQGDSLRSNYANWYQQKPGQAPVLVIYGQ
FNLPSGIPDRFSGSSSGNTASLTITGAQAADEADYYCDSRVSTGIHVVFG
GGTKLTVLG

In some embodiments, the antibody or antigen binding fragment thereof comprises a light chain amino acid sequence set forth in SEQ ID NO: 21:

MGWSWILLFLLSVTAGVHSSSELTQDPAVSVALGQTVRITCQGDSLRSNY
ANWYQQKPGQAPVLVIYGQFNLPSGIPDRFSGSSSGNTASLTITGAQAAD
EADYYCDSRVSTGIHVVFGGGTKLTVLGQPKAAPSVTLFPPSSEELQANK
ATLVCLISDFYPGAVTVAWKADSSPVKAGVETTTPSKQSNNKYAASSYLS
LTPEQWKSHRSYSCQVTHEGSTVEKTVAPTECS

It is understood that antibodies and antigen binding fragments described above, whether specified in terms of heavy and light chain components, or heavy or light chain components, can have any of the functional properties and activities described herein.

In some embodiments, the full length heavy or light chain, variable region, CDR, framework region, or constant region of an antibody or antigen binding fragment described herein can have at least 80% sequence identity (e.g., at least 85%, 90%, 95%, 97%, 98%, 99%, or 100% sequence identity) to the corresponding amino acid sequence set forth in any one of SEQ ID Nos: 1-9, 11, 12, and 14-21. The percent identity between a particular amino acid sequence and the amino acid sequence set forth in any one of SEQ ID Nos: 1-9, 11, 12, and 14-21 and can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from the U.S. government's National Center for Biotechnology Information web site. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1 .txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison will present those regions of homology as aligned sequences. If the two compared sequences do not share homology, then the designated output file will not present aligned sequences. Similar procedures can be followed for nucleic acid sequences except that blastn is used.

Once aligned, the number of matches is determined by counting the number of positions where an identical amino acid residue is presented in both sequences. The percent identity is determined by dividing the number of matches by the length of the amino acid sequence in SEQ ID NOs: 1-9, 11, 12, and 14-21, followed by multiplying the resulting value by 100.

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode the amino acid sequences set forth in SEQ ID NOs: 1-9, 11, 12, and 14-21. The degeneracy of the genetic code is well known to the art; i.e., for many amino acids, there is more than one nucleotide triplet that serves as the codon for the amino acid. The nucleotide sequence encoding the amino acid sequence of SEQ ID NO: 9 is set forth in SEQ ID NO: 10. The nucleotide sequence encoding the amino acid sequence of SEQ ID NO: 12 is set forth in SEQ ID NO: 13. In some embodiments, a heavy or light chain of an antibody is encoded by a nucleic acid having at least 80% sequence identity (e.g., at least 85%, 90%, 95%, 97%, 98%, 99%, or 100% sequence identity) to the nucleotide sequences set forth in SEQ ID NOs.: 10 and 13. Sequence identity is calculated as described above for protein sequences except that blastn is used.

In one embodiment, an antibody or antigen birding fragment thereof described herein can be de-fucosylated.

In some embodiments, an antibody or antigen binding fragment thereof described herein induces antibody-dependent cell-mediated cytotoxicity (ADCC) of FRβ expressing target cells. Suitable antigen binding fragments that induce ADCC have a functional Fc region, i.e., an Fc region that can bind to an Fc receptor on an ADCC effector cell. The antibodies and antigen binding fragments thereof can bind to IgG Fc binding receptors (FcγR) receptors I, II and III (CD64, CD32, and CD16) in order to mediate the functional activities described herein. In some embodiments, binding to a FcγR (e.g., FcγR III) can be enhanced by removing fucose residues from and/or by increasing galactosylation of the glycan present on the Fc portion of an $IgG_1$. See, for example, Houdes et al., Molecular & Cellular Proteomics 9:1716-1728 (2010); Kubota et al., Cancer Sci., 100: 1566-1572 (2009); Malphettes et al., Biotechnol. Bioeng., 106: 774-783 (2010); and Raju, Curr. Opin. Immunol., 20:471-478 (2008).

De-fucosylated antibodies can be produced using, for example, cells with reduced expression of the GDP-4,6-dehydratase gene (e.g., from a mutation such as that in Chinese hamster ovary (CHO) Lec13 cells or from a small interfering RNA against the GDP-4,6-dehydratase gene), cells in which the .alpha.-1,6-fucosyltransferase (FUT8) has been knocked out or expression reduced (e.g., using a small interfering RNA (siRNA) against the FUT8 gene), cells co-expressing β-1,4-N-acetylglucosaminyltransferase III (GnT-III) and Golgi α mannosidase II (ManII), or cells expressing GDP-6-deoxy-D-lyxo-4-hexylose reductase (RMD). See, Ishiguro et al., Cancer Sci., pages 1-7, July, 2010; and von Horsten, Glycobiology, published online Jul. 23, 2010. FcγR binding also can be enhanced by mutating relevant amino acids in the heavy chain constant regions comprising the Fc region (e.g., the hinge region, the $C_H2$ region, or the $C_H3$ region). See, for example, Natsume et al., Drug Des. Develop. Ther., 3:7-16 (2009). In some embodiments, an antibody or fragment thereof can induce opsonization-mediated clearance and/or induce complement-mediated lysis of FRβ expressing target cells. ADCC can be assessed in vitro using a lactate dehydrogenase (LDH) release assay or chromium-51 release assay.

In another embodiment, the disclosure relates to FRβ binding agents or antibodies that bind to particular epitopes of FRβ that contain, for example, at least three amino acids of human FRβ (FIG. 1, SEQ ID NO: 22). For example, an epitope can contain 3 to 30 such as 5 to 25, 7 to 23, 10 to 20, or 13 to 18 amino acids of human FRβ). For example, an epitope can contain 3, 4, 5, 6, 7, 8, 9, 10, 11, 12, 13, 14, 15, 16, 17, 18, 19, 20, 21, 22, 23, 24, 25, 26, 27, 28, 29, or 30 amino acids of human FRβ. The epitope can be in the N-terminal half (i.e., residues 1 to 127 of SEQ ID NO: 9) or the C-terminal half of human FRβ (i.e., residues 128 to 255 of SEQ ID NO:22).

In certain embodiments, a FRβ-binding agent or antibody described herein can be conjugated or linked, either covalently or noncovalently, to a variety of molecules, including pharmaceutical agents, liposomes, oligonucleotides (e.g., small interfering RNA (siRNA)), toxins, detectable moieties, or biological molecules (e.g., a cytokine such as an interleukin (IL) 2, IL4, IL 12, 13 or 15; interferon (IFN), IFNα, IFNβ, or IFNγ) using methods known in the art. Conjugating or linking such molecules to an antibody or antigen binding fragment described herein allows the molecule to be targeted specifically to FRβ. As such, molecules can be delivered to the desired site while minimizing toxicity.

For example, an antibody or antigen binding fragment can be conjugated with a pharmaceutical agent such as a chemotherapeutic (e.g., cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, or an analog of any of the aforementioned). An antibody or antigen binding fragment also can be conjugated with an anti-inflammatory agent such as a glucocorticoid, nonsteroidal anti-inflammatory agent, phosphoinositide-3-kinase inhibitor (e.g., wortmannin or derivatives such as demethoxyviridin, PX-866, LY294002, and LY294002 RGDS (Arg-Gly-Asp-Ser)-conjugated pro-drug SF1126, see, e.g., Maira et al., Biochem. Soc. Trans., 37, 265-272 (2009)); NF-kappa-B inhibitor, I-kappa-B kinase inhibitor, mTOR (mammalian target of rapamycin) inhibitor (e.g., rapamycin, CCl-779, RAD001, or AP23573, see Maira et al., supra), mitogen activated protein (MAP) kinase inhibitor (e.g., SB-203580 and VX-745, see Brown et al., J. Inflammation, 5:22 (2008), or a Janus kinase (JAK) inhibitor.

In some embodiments, an antibody or antigen binding fragment also can be conjugated with a liposome. See, for example, the nanoliposomes of Low et al. (Accounts of Chemical Research, 41(1):120-129 (2008)) that are less than 100 nm in diameter and contain a portion of PEGylated lipids (i.e., a lipid linked to polyethylene glycol (PEG)). Liposomes can be loaded with a pharmaceutical agent using methods known in the art.

In certain embodiments, an antibody or antigen binding fragment described herein can be linked to a toxin such as Pseudomonas exotoxin A (PE), diphtheria toxin (DT), gelonin, saporin, ricin A, abrin, mistletoe lectin, modeccin, pokeweed antiviral protein (PAP), Bryodin 1, bouganin, or biologically active fragments thereof, to generate an immunotoxin. See, for example, Kreitman, BioDrugs, 23(1):1-13 (2009). PE and DT, and biologically active fragments thereof, are particularly useful. A biologically active fragment of PE can include, for example, amino acids 253-364 and 381-613 of PE as described by Hassan et al., J Immunother., 23:473-9 (2000). A biologically active fragment of DT can include DT388 or DAB389, which contain the first 388 or 389 amino acids of DT. See, for example, Chaudhary et al., Biochem Biophys Res Commun., 180:545-51 (1991). Such immunotoxins are useful for killing FRβ expressing cells (e.g., any of the cancer cells described herein) in vivo or in vitro.

In certain embodiments, an antibody or antigen binding fragment described herein can be linked to a detectable moiety. Suitable detectable moieties include, without limitation, radionuclides (e.g., radionuclides used for in vivo diagnostics such as $^{186}$Re, $^{188}$Re, $^{64}$Cu, $^{67}$Cu, $^{212}$Bi, $^{123}$I, $^{131}$I, $^{211}$At, $^{177}$Lu, $^{47}$Sc, $^{105}$Rh, $^{109}$Pd, $^{153}$Sm, $^{199}$Au, $^{99m}$Tc, $^{111}$In, $^{124}$I, $^{18}$F, $^{11}$C, $^{198}$Au, $^{75}$Br, $^{76}$Br, $^{77}$Br, $^{13}$N, $^{34m}$Cl, $^{38}$Cl, $^{52m}$Mn, $^{55}$Co, $^{62}$Cu, $^{68}$Ga, $^{72}$As, $^{76}$As, $^{72}$Se, $^{73}$Se, or $^{75}$Se, or radionuclides useful for in vitro experiments such as 125I, $^{35}$S, $^{3}$H, $^{32}$P, $^{33}$P, or $^{14}$C), fluorescent moieties (e.g., fluorescein, fluorescein isothiocyanate (FITC), PerCP, rhodamine, or phycoerythrin (PE)), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a detectable moiety depend on the nature of the moiety and are known in the art. Examples of detectors include, without limitation, x-ray film, radioactivity counters, scintillation counters, spectrophotometers, colorimeters, fluorometers, luminometers, and densitometers. Methods of attaching the radionuclide atoms (or larger molecules/chelates containing them) to an antibody or antigen binding fragment thereof are known in the art and can include incubating the antibody or fragment thereof with the radionuclide under conditions (e.g., pH, salt concentration, and/or temperature) which facilitate binding of the radionuclide atom or radionuclide atom-containing molecule or chelate to the antibody or antigen binding fragment (see, e.g., U.S. Pat. No. 6,001,329).

Other examples of detectable moieties that can be linked to an antibody or antigen binding fragment include imaging agents, such as MRI or computed tomography (CT) contrast agents. Non-limiting examples of MRI contrast agents include gadolinium and manganese chelates, iron salts, or gadolinium compounds such as gadodiamide (OMNISCA™), gadobenic acid (MULTIHANCE™), gadopentetic acid (MAGNAVIST™), gadoteridol (PROHANCE™) gadofosveset (ABLAVAR™), gadoversetamide (OPTIMARK™), or gadoxetic acid (EOVIST™, known). Non-limiting examples of CT contrast agents include iodine based agents such as UROGRAFIN™, TELEBRIX™, GASTROGRAFIN™, OMNIPAQUE™, ULTRAVIST™, or VISIPAQUET™.

In one embodiment, the disclosure relates to a genetically engineered construct comprising an antibody or antibody fragment thereof disclosed herein. In one embodiment, the disclosure relates to a genetically engineered construct comprising AS04498 or a fragment thereof.

In some embodiments, the disclosure relates to chimeric antigen receptor having an antibody or fragment thereof disclosed herein. Chimeric antigen receptors, or CARs, are recombinant receptor constructs composed of an extracellular single-chain variable fragment (scFv) derived from an antibody, joined to a hinge/spacer peptide and a transmembrane domain, which is further linked to the intracellular T cell signaling domains of the T cell receptor. CAR T cells combine the specificity of an antibody with the cytotoxic and memory functions of I cells.

In some embodiments, a nucleic acid encoding an antibody or an antigen binding fragment such as an scFv fragment is included in a construct for producing a chimeric immune receptor. Chimeric immune receptors typically include an extracellular portion and an intracellular portion, where the extracellular portion is an antigen binding fragment (e.g., a scFv fragment) having binding affinity for human FRβ and the intracellular portion is at least the intracellular domain of a signaling polypeptide such as the CD3 zeta chain, FcRγ chain, or a kinase such as a Syk cytoplasmic phosphotyrosine kinase. A chimeric immune receptor further can include at least the intracellular domain of a costimulatory polypeptide such as the intracellular domain of CD28 or other costimulatory polypeptide such as OX40 (CD134), CD40L, PD-1, or 4-1BB (CD137).

In some embodiments, a chimeric immune receptor includes an scFv fragment fused to the nonligand binding part of the extracellular and the entire transmembrane and intracellular domains of CD28, which is fused with the intracellular domain of FcRγ. Constructs encoding chimeric immune receptors can be introduced ex vivo (e.g., using a retroviral vector) into T cells (e.g., cytotoxic T cells, CD4+ T cells, or CD8+ T cells) from peripheral lymphocytes of a given patient, and the resulting engineered T cells containing the chimeric receptor can be re-introduced into the patient. The engineered T cells can produce at least one cytokine or lymphokine (e.g., IL2, IL3, IL4, IL5, IL6, IL9, IL10, IL12, or IFN-gamma.). Upon binding of the engineered T cells to FRβ expressing target cells, the engineered T cells are activated and can kill the FRβ expressing target cells. See, for example, Eshhar in "Therapeutic Antibodies. Handbook of Experimental Pharmacology 181" Y. Chernajovsky, A. Nissim (eds.), 2008; and Pienert et al., Immunotherapy, 1(6): 905-912 (2009).

In one embodiment, the disclosure relates to a CAR and the nucleic acid sequence encoding the CAR, wherein the CAR comprises an antigen binding domain, a transmembrane domain, a costinniiatory signaling region, and a CD3 zeta signaling domain, wherein the antigen binding domain is a FR1 binding agent. In one embodiment, the FR-β binding agent is AS04498.

In certain embodiments, the FRβ-binding agent or antibody binds FRβ protein with a equilibrium dissociation constant ($K_D$) of about 1 μM or less, about 100 nM or less, about 40 nM or less, about 20 nM or less, about 10 nM or less, about 1 nM or less, or about 0.1 nM or less. In some embodiments, a FRβ-binding agent or antibody binds FRβ with a $K_D$ of about 2.5 nM or less. In some embodiments, a FRβ-binding agent or antibody binds FRβ with a $K_D$ of about 0.1 nM or less. In some embodiments, the dissociation constant of the binding agent (e.g., an antibody) to a FRβ protein is the dissociation constant determined using a FRβ fusion protein comprising at least a portion of the FRβ protein immobilized on a Biacore chip.

In one embodiment, the FRβ-binding agent is AS04498 with a $K_D$ of 2.5 nM. The reported $K_D$ for m909 is 57 nM.

In one embodiment, the FRβ-binding agent is an isolated, fully human monoclonal antibody that binds FRβ with a $K_D$ of less than 2.5 nM.

In one embodiment, the FRβ-binding agent is an isolated, fully human monoclonal antibody that binds FRβ with a $K_D$ from about 2.5 nM to about 50 nM.

In certain embodiments, the FRβ-binding agent (e.g., an antibody) binds to human FRβ protein with a half maximal effective concentration ($EC_{50}$) of about 1 μM or less, about 100 nM or less, about 40 nM or less, about 20 nM or less, about 10 nM or less, about 1 nM or less, or about 0.1 nM or less.

In certain embodiments, the FRβ-binding agent is a recombinant antibody. In some embodiments, the antibody is a monoclonal antibody. In some embodiments, the antibody is a chimeric antibody. In some embodiments, the antibody is a humanized antibody. In some embodiments, the antibody is a fully human antibody. In some embodiments, the antibody is fully human, man-made antibody.

In certain embodiments, the antibody is an IgG1 antibody. In certain embodiments, the antibody is an IgG2 antibody. In certain embodiments, the antibody is an antibody fragment comprising an antigen-binding site. In some embodiments, the antibody is monovalent, monospecific, bivalent, bispecific, or multispecific. In some embodiments, the antibody is conjugated to a cytotoxic moiety. In some embodiments, the antibody is isolated. In some embodiments, the antibody is substantially pure.

The FRβ-binding agents (e.g., antibodies) disclosed herein can be assayed for specific binding by any method known in the art. The immunoassays that can be used include, but are not limited to, competitive and non-competitive assay systems using techniques such as Biacore analysis, FACS analysis, immunofluorescence, immunocytochemistry, Western blots, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are routine and well-known in the art (see, e.g., Ausubel et al., Editors, 1994-present, Current Protocols in Molecular Biology, John Wiley & Sons, Inc., New York, N.Y.).

For example, the specific binding of an antibody to human FRβ may be determined using ELISA. An ELISA assay comprises preparing antigen, coating wells of a 96 well microtiter plate with antigen, adding the FRβ-binding antibody or other FRβ-binding agent conjugated to a detectable compound such as an enzymatic substrate (e.g. horseradish peroxidase or alkaline phosphatase) to the well, incubating for a period of time and detecting the presence of the antibody bound to the antigen. In some embodiments, the FRβ-binding antibody or agent is not conjugated to a detectable compound, but instead a second conjugated antibody that recognizes the FRβ-binding antibody or agent is added to the well. In some embodiments, instead of coating the well with the antigen, the FRβ-binding antibody or agent can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art.

In another example, the specific binding of an antibody to human FRβ may be determined using FACS. A FACS screening assay may comprise generating a cDNA construct that expresses an antigen as a fusion protein (e.g., FRβ-Fc or FRβ-CD4TM), transfecting the construct into cells, expressing the antigen on the surface of the cells, mixing the FRβ-binding antibody or other FRβ-binding agent with the transfected cells, and incubating for a period of time. The cells bound by the FRβ-binding antibody or other FRβ-binding agent may be identified by using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of an antibody or other binding-agent to an antigen (e.g., a FRβ protein) and the off-rate of an antibody-antigen interaction can be determined by competitive binding assays. One example of a competitive binding assay is a radioimmunoassay comprising the incubation of labeled antigen (e.g., $^{3}H$ or $^{125}I$), or fragment or variant thereof, with the antibody of interest in the presence of increasing amounts of unlabeled antigen followed by the detection of the antibody bound to the labeled antigen. The affinity of the antibody for an antigen (e.g., a FRβ protein) and the binding off-rates can be determined from the data by Scatchard plot analysis. In some embodiments, Biacore kinetic analysis is used to determine the binding on and off rates of antibodies or agents that bind an antigen (e.g., a FRβ protein). Biacore kinetic analysis comprises analyzing the binding and dissociation of antibodies from chips with immobilized antigen (e.g., a FRβ protein) on their surface.

IV. Methods of Using a FRβ Binding Agent or Antibody

In one embodiment, a FRβ binding agent, such as a human anti-human FRβ mAb or antigen binding fragment thereof, is administered to a mammal, such as a human, with cells expressing FRβ. In one embodiment, a FRβ binding agent, such as a human anti-human FRβ mAb or antigen binding fragment thereof, is administered to a mammal, such as a human, with macrophages expressing FRβ. In one embodiment, a FRβ binding agent, such as a human anti-human FRβ mAb or antigen binding fragment thereof, is administered to a mammal, such as a human, with activated macrophages expressing FRβ.

In one embodiment, a FRβ binding agent, such as a human anti-human FRβ mAb or antigen binding fragment thereof, is administered to a mammal such as a human that has been diagnosed with an inflammatory disorder or a cancer expressing cell surface FRβ. In some embodiments, engineered T cells containing a chimeric immune receptor (see above section) are administered to the human patient. Non-limiting examples of inflammatory disorders include atherosclerosis, ischemia/reperfusion injury, transplantation rejection, vasculitis such as Wegener's granulomatosus, inflammatory osteoarthritis, glomerulonephritis, restenosis, systemic sclerosis, fibromyalgia, sarcoidosis, and autoimmune diseases. Non-limiting examples of autoimmune diseases include rheumatoid arthritis, systemic lupus erythematosus (SLE), ulcerative colitis, psoriasis, Type 1 diabetes (insulin-dependent diabetes mellitus), Crohn's disease, multiple sclerosis, and Sjogren's disease. Inflammatory disorders also can include obstructive pulmonary diseases such as asthma or chronic obstructive pulmonary disease (COPD), and Idiopathic Pulmonary Fibrosis (IPF).

In one embodiment, a FRβ binding agent, such as a human anti-human FRβ mAb or fragments described herein also can be administered to a subject suspected of having an inflammatory disorder. A subject "suspected of having an inflammatory disorder" is one having one or more signs of the disorder. Signs of such disorders are well-known to those of skill in the art and include, without limitation, redness, swelling (e.g., swollen joints), skin rashes, joint pain, joint pain, loss of joint function, fever, chills, fatigue, loss of energy, headaches, loss of appetite, muscle stiffness, insomnia, itchiness, stuffy nose, sneezing, coughing, or one or more neurologic symptoms such as weakness, paresthesias, paralysis, dizziness, seizures, or pain. Signs of diabetes include, without limitation, higher than normal frequency of urination, unusual thirst, extreme hunger, unusual weight loss, extreme fatigue, visual problems, and irritability.

Non-limiting examples of cancers expressing cell surface FRβ include myeloid cancers such as acute myeloid leukemia (AML) or chronic myeloid leukemia (CML), multiple myeloma, or a solid cancer containing FRβ expressing cells such as squamous cell carcinoma of the head and neck, or a malignancy of non-epithelial origin. Treatment of an inflammatory disorder or cancer can include reducing the severity of the disorder or slowing progression of the disorder.

In one embodiment, a FRβ binding agent, such as a human anti-human FRβ mAb or antigen binding fragment thereof, also can be administered prophylactically in subjects at risk for developing an inflammatory disorder to prevent development of symptoms of the disorder from occurring, delay onset of symptoms, or lessen the severity of subsequently developed disorder symptoms. A subject "at risk of developing an inflammatory disorder" refers to a subject with a family history of one or more inflammatory disorders (e.g., a genetic predisposition to one or more inflammatory disorders) or one exposed to one or more inflammation-inducing conditions.

For example, a subject can have been exposed to a viral or bacterial superantigen such as, but not limited to, Staphylococcal enterotoxins (SEs), a *Streptococcus pyogenes* exotoxin (SPE), a *Staphylococcus aureus* toxic shock-syndrome toxin (TSST-1), a Streptococcal mitogenic exotoxin (SME) and a Streptococcal superantigen (SSA). A FRβ binding agent, such as a human anti-human FRβmAb or fragment thereof also can be administered to deplete activated macrophages from a human subject. In any case, an amount of a FRβ binding agent, such as a human anti-human FRβmAb or antigen binding fragment thereof effective to reduce the number of FRβ positive cells (e.g., macrophages and monocytes, or cancer cells) in the patient is administered. The number of FRβ positive cells can be determined by doing cell counts or using a folate-targeted imaging agent.

Methods described herein can include, for example, monitoring the patient to determine if the disorder is improving with treatment. Any method can be used to monitor an inflammatory disorder or cancer. For example, for rheumatoid arthritis patients, joint pain and/or stiffness, or bone erosion can be monitored in the patient. For cancer patients, tumor size, cell count, or cancer specific markers can be monitored.

In one embodiment, the disclosure provides methods for inhibiting growth of a tumor using the FRβ-binding agents or antibodies described herein. In certain embodiments, the method of inhibiting growth of a tumor comprises contacting a cell with a FRβ-binding agent (e.g., antibody) in vitro. For example, an immortalized cell line or a cancer cell line is cultured in medium to which is added an anti-FRβ antibody or other agent to inhibit tumor growth. In some embodiments, tumor cells are isolated from a patient sample such as, for example, a tissue biopsy, pleural effusion, or blood sample and cultured in medium to which is added a RSPO-binding agent to inhibit tumor growth.

In some embodiments, the method of inhibiting growth of a tumor comprises contacting the tumor or tumor cells with a RSPO-binding agent (e.g., antibody) in vivo.

In certain embodiments, the method of inhibiting growth of a tumor comprises administering to a subject a therapeutically effective amount of a FRβ-binding agent. In certain embodiments, the subject is a human. In certain embodiments, the subject has a tumor or has had a tumor which was removed. In some embodiments, the subject has a tumor with an elevated expression level of FRβ. In some embodiments, the FRβ-binding agent is an antibody. In some embodiments, the FRβ-binding agent is antibody AS04498.

In certain embodiments, the tumor has elevated expression levels of FRβ or over-expresses FRβ. In some embodiments, the tumor has a high expression level of FRβ. In general, the phrase "a tumor has elevated expression levels of" a protein (or similar phrases) refers to expression levels of a protein in a tumor as compared to expression levels of the same protein in normal tissue of the same tissue type. However, in some embodiments, the expression levels of a protein in a tumor are "elevated" or "high" as compared to the average expression level of the protein within a group of tissue types. In some embodiments, the expression levels of a protein in a tumor are "elevated" or "high" as compared to the expression level of the protein in other tumors of the same tissue type or a different tissue type.

In certain embodiments, the disclosure provides a method of inhibiting growth of a tumor in a subject, comprising administering a therapeutically effective amount of a FRβ-binding agent to the subject. In certain embodiments, the tumor comprises cancer stem cells. In certain embodiments, the frequency of cancer stem cells in the tumor is reduced by administration of the FRβ-binding agent. In some embodiments, the disclosure also provides a method of reducing the frequency of cancer stem cells in a tumor, comprising contacting the tumor with an effective amount of a FRβ-binding agent (e.g., an anti-FRβ antibody).

In some embodiments, the tumor is a solid tumor. In certain embodiments, the tumor is a tumor selected from the group consisting of colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In some embodiments, the tumor is a colorectal tumor that comprises an inactivating mutation in the APC gene. In some embodiments, the tumor is a colorectal tumor that does not comprise an inactivating mutation in the APC gene.

In certain embodiments, the disclosure provides methods for treating cancer comprising administering a therapeutically effective amount of a FRβ-binding agent to a subject. In certain embodiments, the cancer is characterized by cells expressing elevated levels of FRβ protein as compared to expression levels of FRβ protein in normal tissue. In certain embodiments, the cancer is characterized by cells over-expressing FRβ.

In certain embodiments, in addition to administering a FRβ-binding agent (e.g., an antibody), the method or treatment further comprises administering at least one additional therapeutic agent. An additional therapeutic agent can be administered prior to, concurrently with, and/or subsequently to, administration of the FRβ-binding agent. Pharmaceutical compositions comprising a FRβ-binding agent and the additional therapeutic agent(s) are also provided. In some embodiments, the at least one additional therapeutic agent comprises 1, 2, 3, or more additional therapeutic agents.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistant cancer cells will develop. In some embodiments, combination therapy comprises a therapeutic agent that affects (e.g., inhibits or kills) non-tumorigenic cells and a therapeutic agent that affects (e.g., inhibits or kills) tumorigenic CSCs.

In some embodiments, the combination of a FRβ-binding agent and at least one additional therapeutic agent results in additive or synergistic results. In some embodiments, the combination therapy results in an increase in the therapeutic index of the FRβ-binding agent. In some embodiments, the combination therapy results in an increase in the therapeutic index of the additional agent(s). In some embodiments, the combination therapy results in a decrease in the toxicity and/or side effects of the FRβ-binding agent. In some embodiments, the combination therapy results in a decrease in the toxicity and/or side effects of the additional agent(s).

Useful classes of therapeutic agents include, for example, antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an antimetabolite, an antimitotic, a topoisomerase inhibitor, or an angiogenesis inhibitor. In some embodiments, the second therapeutic agent is a platinum complex such as carboplatin or cisplatin. In some embodiments, the additional therapeutic agent is a platinum complex in combination with a taxane.

Therapeutic agents that may be administered in combination with the RSPO-binding agents include chemotherapeutic agents, representative, non-limiting examples of chemotherapeutic agents are recited above. Thus, in some embodiments, the method or treatment involves the administration of a FRβ-binding agent or antibody disclosed herein in combination with a chemotherapeutic agent or cocktail of multiple different chemotherapeutic agents.

Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in. The Chemotherapy Source Book, $4^{th}$ Edition, 2008, M. C. Perry, Editor, Lippincott, Williams & Wilkins, Philadelphia, Pa.

Combined administration can include co-administration, either in a single pharmaceutical formulation or using separate formulations, or consecutive administration in either order but generally within a time period such that all active agents can exert their biological activities simultaneously.

It will be appreciated that the combination of a FRβ-binding agent and at least one additional therapeutic agent may be administered in any order or concurrently. In some embodiments, the FRβ-binding agent will be administered to patients that have previously undergone treatment with a second therapeutic agent. In certain other embodiments, the FRβ-binding agent and a second therapeutic agent will be administered substantially simultaneously or concurrently. For example, a subject may be given a FRβ-binding agent (e.g., an antibody) while undergoing a course of treatment with a second therapeutic agent (e.g., chemotherapy). In certain embodiments, a FRβ-binding agent will be administered within 1 year of the treatment with a second therapeutic agent. In certain alternative embodiments, a FRβ-binding agent will be administered within 10, 8, 6, 4, or 2 months of any treatment with a second therapeutic agent. In certain other embodiments, a FRβ-binding agent will be administered within 4, 3, 2, or 1 weeks of any treatment with a second therapeutic agent. In some embodiments, a FRβ-binding agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of an FRβ-binding agent (e.g., an antibody) disclosed herein depends on the type of disease to be treated, the severity and course of the disease, the responsiveness of the disease, whether the FRβ-binding agent or antibody is administered for therapeutic or preventative purposes, previous therapy, the patient's clinical history, and so on, all at the discretion of the treating physician. The FRβ-binding agent or antibody can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody or agent. The administering physician can easily determine optimum dosages, dosing methodologies, and repetition rates. In certain embodiments, dosage is from 0.01 μg to 100 mg/kg of body weight, from 0.1 μg to 100 mg/kg of body weight, from 1 μg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In certain embodiments, the dosage of the antibody or other FRβ-binding agent is from about 0.1 mg to about 20 mg/kg of body weight. In certain embodiments, dosage can be given once or more daily, weekly, monthly, or yearly. In certain embodiments, the antibody or other FRβ-binding agent is given once every week, once every two weeks or once every three weeks.

In some embodiments, a FRβ-binding agent (e.g., an antibody) may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

Thus, the disclosure provides methods of treating cancer in a subject comprising using an intermittent dosing strategy for administering one or more agents, which may reduce side effects and/or toxicities associated with administration of a FRβ-binding agent, chemotherapeutic agent, etc. In some embodiments, a method for treating cancer in a human subject comprises administering to the subject a therapeutically effective dose of a FRβ-binding agent in combination with a therapeutically effective dose of a chemotherapeutic agent, wherein one or both of the agents are administered according to an intermittent dosing strategy. In some embodiments, the intermittent dosing strategy comprises administering an initial dose of a FRβ-binding agent to the subject, and administering subsequent doses of the FRβ-binding agent about once every 2 weeks.

In some embodiments, the intermittent dosing strategy comprises administering an initial dose of a FRβ-binding agent to the subject, and administering subsequent doses of the FRβ-binding agent about once every 3 weeks. In some embodiments, the intermittent dosing strategy comprises administering an initial dose of a FRβ-binding agent to the subject, and administering subsequent doses of the FRβ-binding agent about once every 4 weeks. In some embodiments, the FRβ-binding agent is administered using an intermittent dosing strategy and the chemotherapeutic agent is administered weekly.

In certain embodiments, a FRβ binding agent, such as a human anti-human FRβ mAb or antibody fragments described herein (with or without linked moieties) may be administered by any available route including, but not limited to, oral or parenteral routes of administration such as intravenous, intramuscular, intraperitoneal, subcutaneous, intrathecal, intraarterial, nasal, transdermal (e.g., as a patch), or pulmonary absorption. Antibodies or antibody fragments may include a delivery agent (e.g., a cationic polymer, peptide molecular transporter, surfactant, etc.) as a composition containing a pharmaceutically acceptable carrier. As used herein the term "pharmaceutically acceptable carrier" includes solvents, dispersion media, coatings, antibacterial and antifugal agents, isotonic and absorption delaying agents, and the like, compatible with pharmaceutical administration. Supplementary active compounds can also be incorporated into pharmaceutical formulations as described herein.

A pharmaceutical composition is formulated to be compatible with its intended route of administration. Solutions or suspensions used for parenteral administration can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® ELTM (BASF, Parsippany, N.J.) or phosphate buffered saline (PBS). In all cases, the composition should be sterile and should be fluid to the extent that easy syringability exists. Pharmaceutical formulations are ideally stable under the conditions of manufacture and storage and should be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the antibody or antibody fragment in the required amount in an appropriate solvent with one or a combination of ingredients enumerated above, as required, followed by filtered sterilization. Generally, dispersions are prepared by incorporating the purified antibody or antibody fragment into a sterile vehicle which contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the antibody or antibody fragment can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the a FRβ-binding agent, such as a human anti-human FRβ mAb or antibody fragment thereof and a delivery agent are preferably delivered in the form of an aerosol spray from a pressured container or dispenser which contains a suitable propellant, e.g., a gas such as carbon dioxide, or a nebulizer. The present disclosure particularly contemplates delivery of the compositions using a nasal spray, inhaler, or other direct delivery to the upper and/or lower airway. According to certain embodiments, a FRβ-binding agent, such as a human anti-human FRβ mAb or antibody fragment thereof and a delivery agent are formulated as large porous particles for aerosol administration.

Systemic administration also can be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified polypeptide or protein and delivery agents are formulated into ointments, salves, gels, or creams as generally known in the art.

In certain embodiments, compositions are prepared with carriers that will protect the antibody or antibody fragment against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active antibody or antibody fragment calculated to produce the desired therapeutic effect in association with the required pharmaceutical carrier.

In certain embodiments, the a FRβ-binding agent, such as a human anti-human FRβ mAb or antibody fragment can be administered at various intervals and over different periods of time as required. Those of ordinary skill in the art will appreciate that certain factors can influence the dosage and timing required to effectively treat a subject, including but not limited to the severity of the disease or disorder, previous treatments, the general health and/or age of the subject, and other diseases present. Generally, treatment of a subject with a FRβ-binding agent, such as a human anti-human FRβ mAb or antibody antigen-binding fragment as described herein can include a single treatment or, in many cases, can include a series of treatments. It is furthermore understood that appropriate doses may depend upon the potency of the antibody or antibody fragment and may optionally be tailored to the particular recipient, for example, through administration of increasing doses until a preselected desired response is achieved. It is understood that the specific dose level for any particular animal subject may depend upon a variety of factors including the activity of the specific polypeptide or protein employed, the age, body weight, general health, gender, and diet of the subject, the time of administration, the route of administration, the rate of excretion, any drug combination, and the degree of expression or activity to be modulated.

Pharmaceutical formulations as described herein can be included in a container, pack, or dispenser together with instructions for administration.

In some embodiments, an antibody or antigen binding fragment thereof is administered in combination with one or more pharmaceutical agents (e.g., an anti-inflammatory agent) or antibodies.

V. Kits Comprising FRβ-Binding Agents

The disclosure provides kits that comprise the FRβ-binding agents (e.g., antibodies) described herein and that can be used to perform the methods described herein. In certain embodiments, a kit comprises at least one purified antibody against FRβ protein in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed FRβ-binding agents can be readily incorporated into one of the established kit formats that are well known in the art.

Further provided are kits comprising a FRβ-binding agent (e.g., an anti-FRβ antibody), as well as at least one additional therapeutic agent. In certain embodiments, the second (or more) therapeutic agent is a chemotherapeutic agent. In certain embodiments, the second (or more) therapeutic agent is an angiogenesis inhibitor.

The disclosure is further described by the following paragraphs:

1. An isolated human monoclonal antibody, or an antigen-binding fragment thereof, that specifically binds human folate receptor beta (FRβ), the antibody or fragment comprising: a heavy chain variable region ($V_H$) CDR 1 comprising the amino acid sequence set forth in SEQ ID NO:1; a $V_H$ CDR2 comprising the amino acid sequence set forth in SEQ ID NO:2; a $V_H$ CDR3 comprising the amino acid sequence set forth in SEQ ID NO:3; a light chain variable region ($V_L$) CDR1 comprising the amino acid sequence set forth in SEQ ID NO:4; a $V_L$ CDR2 comprising the amino acid sequence set forth in SEQ ID NO:5; and a $V_L$ CDR3 comprising the amino acid sequence set forth in SEQ ID NO:6.
2. An isolated human monoclonal antibody, or an antigen-binding fragment thereof, that specifically binds human folate receptor beta (FRβ), the antibody or fragment comprising a heavy chain and a light chain, wherein the heavy chain variable region ($V_H$) CDR 1 has the amino acid sequence set forth in SEQ ID NO:1; a $V_H$ CDR2 has the amino acid sequence set forth in SEQ ID NO:2; and a $V_H$ CDR3 has the amino acid sequence set forth in SEQ ID NO:3.
3. An isolated human monoclonal antibody, or an antigen-binding fragment thereof, that specifically binds human folate receptor beta (FRβ), the antibody or fragment comprising a heavy chain and a light chain, wherein the light chain variable region ($V_L$) CDR1 has the amino acid sequence set forth in SEQ ID NO: 4; a $V_L$ CDR2 has the amino acid sequence set forth in SEQ ID NO: 5; and a $V_L$ CDR3 has the the amino acid sequence set forth in SEQ ID NO:6.
4. The antibody or fragment of an antibody disclosed herein, wherein the antibody or fragment has one or more properties selected from the group consisting of: (a) the antibody or fragment does not detectably bind to human folate receptor alpha (FRα); (b) the antibody or fragment binds to human macrophages but not to mouse macrophages; (c) the antibody or fragment has a binding affinity from 1 to 5 nM; and (d) the antibody mediates antibody-dependent cellular cytotoxicity (ADCC) of FR-β expressing target cells.
5. An isolated human monoclonal antibody, or an antigen-binding fragment thereof, that specifically binds human folate receptor beta (FRβ) and has an equilibrium dissociation constant ($K_D$) of less than 2.5 nM.
6. An isolated human monoclonal antibody, or an antigen-binding fragment thereof, that specifically binds human folate receptor beta (FRβ), the antibody or fragment comprising: a heavy chain sequence of SEQ ID NO. 8 and a light chain sequence of SEQ ID NO. 12.
7. An isolated human monoclonal antibody, or an antigen-binding fragment thereof, that specifically binds human folate receptor beta (FRβ), the antibody or fragment comprising: a heavy chain sequence of SEQ ID NO. 7 and a light chain sequence of SEQ ID NO. 15.

8. An isolated human monoclonal antibody, or an antigen-binding fragment thereof, that specifically binds human folate receptor beta (FRβ), the antibody or fragment comprising: a heavy chain sequence of SEQ ID NO. 17 and a light chain sequence of SEQ ID NO. 20.
9. An isolated human monoclonal antibody, or an antigen-binding fragment thereof, that specifically binds human folate receptor beta (FRβ), the antibody or fragment comprising: a heavy chain sequence selected from the group consisting of SEQ ID NO. 7, 8, 9, 17, 18, and 19 and a light chain sequence selected from the group consisting of SEQ ID NO. 11, 12, 15, 16, 20, and 21.
10. An isolated human monoclonal antibody, or an antigen-binding fragment thereof, that specifically binds human folate receptor beta (FRβ) with higher affinity than monoclonal antibody m909.
11. An isolated human monoclonal antibody, or an antigen-binding fragment thereof, that specifically binds human folate receptor beta (FRβ) comprising a heavy chain sequence of SEQ ID NO. 24 with one or more mutations recited in Table 4, and a light chain sequence of SEQ ID NO. 25 with one or more mutations recited in Table 4.
12. The antibody or fragment of any of the preceding paragraphs, wherein said antibody or fragment binds to cell surface FRβ.
13. The antibody or fragment of any of the preceding paragraphs, wherein said antibody is an IgG1 antibody.
14. The antibody or fragment of any of the preceding paragraphs, wherein said antibody or fragment is defucosylated.
15. The antibody or fragment of any of the preceding paragraphs, wherein the fragment is a Fab antibody fragment, a $F(ab')_2$ fragment, or a single chain antibody fragment (scFv).
16. The antibody or fragment of any of the preceding paragraphs, wherein said antibody or fragment is conjugated with a pharmaceutical agent 17. The antibody or fragment of any of the preceding paragraphs, wherein said pharmaceutical agent is a chemotherapeutic.
18. The antibody or fragment of any of the preceding paragraphs, wherein said antibody or fragment is conjugated to a liposome.
19. The antibody or fragment of any of the preceding paragraphs, wherein said liposome comprises a pharmaceutical agent.
20. The antibody or fragment of any of the preceding paragraphs, wherein said antibody or fragment is linked to a toxin.
21. The antibody or fragment of any of the preceding paragraphs, wherein said antibody or fragment thereof is covalently linked to said toxin.
22. The antibody or fragment of any of the preceding paragraphs, wherein said antibody or fragment is linked to a detectable moiety.
23. The antibody or fragment of any of the preceding paragraphs, wherein said detectable moiety is selected from the group consisting of a fluorescent moiety, a luminescent moiety, a radioactive moiety, a CT contrast agent, an MRI contrast agent, and biotin.
24. The antibody or fragment of any of the preceding paragraphs, wherein the antibody or fragment comprises SEQ ID NO:7.
25. The antibody or fragment of any of the preceding paragraphs, wherein the antibody or fragment comprises SEQ ID NO:8.
26. The antibody or fragment of any of the preceding paragraphs, wherein the antibody or fragment comprises SEQ ID NO:9.
27. The antibody or fragment of any of the preceding paragraphs, wherein the antibody or fragment comprises SEQ ID NO:11.
28. The antibody or fragment of any of the preceding paragraphs, wherein the antibody or fragment comprises SEQ ID NO:12.
29. A composition comprising the antibody or fragment of any of the preceding paragraphs and a pharmaceutically acceptable carrier.
30. The antibody an antigen-binding fragment thereof of any of the preceding paragraphs, wherein said antibody mediates antibody-dependent cellular cytotoxicity.
31. A method of treating an inflammatory disorder in a subject, comprising administering to the subject a therapeutically effective amount of a monoclonal antibody that specifically binds human FRβ, the antibody or fragment comprising: (a) a heavy chain variable region ($V_H$) CDR 1 comprising the amino acid sequence set forth in SEQ ID NO:1; a $V_H$ CDR2 comprising the amino acid sequence set forth in SEQ ID NO:2; a $V_H$ CDR3 comprising the amino acid sequence set forth in SEQ ID NO:3; a light chain variable region ($V_L$) CDR1 comprising the amino acid sequence set forth in SEQ ID NO:4; a $V_L$ CDR2 comprising the amino acid sequence set forth in SEQ ID NO:5; and a $V_L$ CDR3 comprising the amino acid sequence set forth in SEQ ID NO:6.
32. A method of treating cancer in a subject, comprising administering to the subject a therapeutically effective amount of a monoclonal antibody that specifically binds human FRβ, the antibody or fragment comprising: (a) a heavy chain variable region ($V_H$) CDR 1 comprising the amino acid sequence set forth in SEQ ID NO:1; a $V_H$ CDR2 comprising the amino acid sequence set forth in SEQ ID NO:2; a $V_H$ CDR3 comprising the amino acid sequence set forth in SEQ ID NO:3; a light chain variable region ($V_L$) CDR1 comprising the amino acid sequence set forth in SEQ ID NO:4; a $V_L$ CDR2 comprising the amino acid sequence set forth in SEQ ID NO:5; and a $V_L$ CDR3 comprising the amino acid sequence set forth in SEQ ID NO:6.
33. A method of reducing the number of FRβ positive cells in a subject, comprising administering to the subject a therapeutically effective amount of a monoclonal antibody that specifically binds human FRβ, the antibody or fragment comprising: (a) a heavy chain variable region ($V_H$) CDR 1 comprising the amino acid sequence set forth in SEQ ID NO:1; a $V_H$ CDR2 comprising the amino acid sequence set forth in SEQ ID NO:2; a $V_H$ CDR3 comprising the amino acid sequence set forth in SEQ ID NO:3; a light chain variable region ($V_L$) CDR1 comprising the amino acid sequence set forth in SEQ ID NO:4; a $V_L$ CDR2 comprising the amino acid sequence set forth in SEQ ID NO:5; and a $V_L$ CDR3 comprising the amino acid sequence set forth in SEQ ID NO:6.
34. A method of reducing the number of FRβ positive macrophages in a subject, comprising administering to the subject a therapeutically effective amount of a monoclonal antibody that specifically binds human FRβ, the antibody or fragment comprising: (a) a heavy chain variable region ($V_H$) CDR 1 comprising the amino acid sequence set forth in SEQ ID NO:1; a $V_H$ CDR2 comprising the amino acid sequence set forth in SEQ ID NO:2; a $V_H$ CDR3 comprising the amino acid sequence set forth in SEQ ID NO:3; a light chain variable region ($V_L$) CDR1 comprising the amino acid sequence set forth in SEQ ID NO:4; a $V_L$ CDR2 comprising the amino acid sequence set forth in SEQ ID NO:5; and a $V_L$ CDR3 comprising the amino acid sequence set forth in SEQ ID NO:6.

35. The method of any of the preceding paragraphs, wherein the antibody is a recombinant antibody, a chimeric antibody, a bispecific antibody, a humanized antibody, an IgG1 antibody, an IgG2 antibody, or an antibody fragment comprising an antigen-binding site.

36. The method of any of the preceding paragraphs, wherein the antibody is a humanized antibody.

37. The method of any of the preceding paragraphs, which comprises administering at least one additional therapeutic agent.

38. The method of any of the preceding paragraphs, wherein the additional therapeutic agent is a chemotherapeutic agent.

39. The method of any of the preceding paragraphs, wherein the additional therapeutic agent is a second antibody.

40. The method of any of the preceding paragraphs, wherein the cancer is selected from the group consisting of acute myeloid leukemia, colorectal cancer, ovarian cancer, pancreatic cancer, leukemia, lung cancer, liver cancer, breast cancer, kidney cancer, prostate cancer, gastrointestinal cancer, melanoma, cervical cancer, bladder cancer, glioblastoma, and head and neck cancer.

41. The method of any of the preceding paragraphs, wherein the cancer has an elevated level of FRβ expression compared to the level of FRβ expression in a corresponding normal tissue.

42. The method of any of the preceding paragraphs, further comprising a step of determining the level of FRβ expression in the cancer prior to administration of the antibody.

43. A method of inhibiting growth of a tumor, comprising contacting the tumor with an effective amount of a monoclonal antibody that specifically binds human FRβ, the antibody or fragment comprising: (a) a heavy chain variable region ($V_H$) CDR 1 comprising the amino acid sequence set forth in SEQ ID NO:1; a $V_H$ CDR2 comprising the amino acid sequence set forth in SEQ ID NO:2; a $V_H$ CDR3 comprising the amino acid sequence set forth in SEQ ID NO:3; a light chain variable region ($V_L$) CDR1 comprising the amino acid sequence set forth in SEQ ID NO:4; a $V_L$ CDR2 comprising the amino acid sequence set forth in SEQ ID NO:5; and a $V_L$ CDR3 comprising the amino acid sequence set forth in SEQ ID NO:6.

44. A method of treating an inflammatory disorder comprising administering to a subject the antibody or fragment thereof described in any one of the preceding paragraphs.

45. A method of treating cancer comprising administering to a subject the antibody or fragment thereof described in any one of the preceding paragraphs.

46. A method of reducing the number of FRβ positive cells in a subject comprising administering to the subject the antibody or fragment thereof described in any one of the preceding paragraphs.

47. A method of reducing the number of FRβ positive macrophages in a subject comprising administering to the subject the antibody or fragment thereof described in any one of the preceding paragraphs.

48. An isolated human monoclonal antibody, or an antigen-binding fragment thereof, that specifically binds human folate receptor beta (FRβ), the antibody or fragment comprising: a heavy chain sequence of SEQ ID NO. 7 and a light chain sequence of SEQ ID NO. 11.

49. An isolated human monoclonal antibody, or an antigen-binding fragment thereof, that specifically binds human folate receptor beta (FRβ), the antibody or fragment comprising: a heavy chain sequence of SEQ ID NO. 8 and a light chain sequence of SEQ ID NO. 11.

50. An isolated human monoclonal antibody, or an antigen-binding fragment thereof, that specifically binds human folate receptor beta (FRβ), the antibody or fragment comprising: a heavy chain sequence of SEQ ID NO. 9 and a light chain sequence of SEQ ID NO. 11.

51. An isolated human monoclonal antibody, or an antigen-binding fragment thereof, that specifically binds human folate receptor beta (FRβ), the antibody or fragment comprising: a heavy chain sequence of SEQ ID NO. 7 and a light chain sequence of SEQ ID NO. 12.

52. An isolated human monoclonal antibody, or an antigen-binding fragment thereof, that specifically binds human folate receptor beta (FRβ), the antibody or fragment comprising: a heavy chain sequence of SEQ ID NO. 8 and a light chain sequence of SEQ ID NO. 12.

53. An isolated human monoclonal antibody, or an antigen-binding fragment thereof, that specifically binds human folate receptor beta (FRβ), the antibody or fragment comprising: a heavy chain sequence of SEQ ID NO. 9 and a light chain sequence of SEQ ID NO. 12.

54. A chimeric antigen receptor comprising: a target element, wherein the target element is an antibody or fragment thereof in any one of the preceding paragraphs, a transmembrane domain, a spacer, a costimulatory domain, and a signaling domain.

55. A fully human, man-made antibody or an antigen-binding fragment thereof, that specifically binds human folate receptor beta (FRβ), the antibody or fragment comprising: a heavy chain variable region ($V_H$) CDR 1 comprising the amino acid sequence set forth in SEQ ID NO:1; a $V_H$ CDR2 comprising the amino acid sequence set forth in SEQ ID NO:2; a $V_H$ CDR3 comprising the amino acid sequence set forth in SEQ ID NO:3; a light chain variable region ($V_L$) CDR1 comprising the amino acid sequence set forth in SEQ ID NO:4; a $V_L$ CDR2 comprising the amino acid sequence set forth in SEQ ID NO:5; and a $V_L$ CDR3 comprising the amino acid sequence set forth in SEQ ID NO:6, wherein the antibody does not exist in nature.

Embodiments of the disclosure can be further defined by reference to the following non-limiting examples, which describe in detail preparation of certain antibodies of the disclosure and methods for using FRβ-binding agents or antibodies of the disclosure. It will be apparent to those skilled in the art that many modifications, both to materials and methods, may be practiced without departing from the scope of the present disclosure.

EXAMPLES

Example 1

Expression of Recombinant FRβ

A nucleic acid encoding a fragment of the human folate receptor beta (FRβ) spanning amino acids 22 to 236 (numbering based on sequence in GenBank Accession No. NP_001107007) was cloned from pcDNA3 to baculovirus transfer vector pAcGP67 via Sma I and EcoRI sites. FIG. 1 contains the amino acid sequence (SEQ ID NO:22) of the FRβ protein. Transfer vector pAcGP67 (BD Biosciences Pharmingen) was co-transfected with BaculoGold™ (BD Biosciences Pharmingen) viral DNA into SF9 insect cells according to the manufacturer's instruction.

Recombinant FRβ protein produced from pAcGP67 had four extra residues (ADPL, SEQ ID NO:23) on the N-terminus and five extra histidine residues on the C-terminus. The recombinant FRβ protein was purified from conditioned medium with a nickel-chelating column, and further purified with a SUPERDEX®75 10/300GL gel filtration column in phosphate buffered saline (PBS). The purified protein was >95% purity as estimated by SDS-PAGE. The recombinant FRβ retained its function of binding to folate.

Example 2

Antibody Selection by Affinity Maturation

A. Paratope Mapping by Alanine Scanning

To determine the contribution of a specific residue to antibody affinity and expression, paratope mapping was performed by alanine scanning method. In brief, the variable domains of heavy chain (VH) of M909 antibody (FIG. 2A, SEQ ID NO. 24) and light chain (VL) of M909 antibody (FIG. 2B, SEQ ID NO. 25) were searched by using NCBI Ig-Blast (http://www.ncbi.nlm.nih.gov/projects/igblast/) and complementarity determining regions (CDRs) were defined by KABAT delineation system. All residues within CDRs were replaced one by one with alanine, or converted to serine if alanine already existed in the sequences, by site-directed mutagenesis. Then all these mutants (65 in total) were expressed by *E. coli* in 96-deep-well plates. The crude protein secreted in medium was analyzed by ELISA for assessment of antigen-antibody binding affinity.

The key residues are summarized in Table 1. Reference to the key residue is in regard to the m909 sequence (FIGS. 2A and 2B, SEQ ID NOS. 24 and 25).

TABLE 1

Key residues identified by paratope mapping

| Location | Significant | Moderate |
|---|---|---|
| CDR-H1 (FIG. 2A) | Y27, Y32 | F29, A33, H35 |
| CDR-H2 (FIG. 2A) | N52 | I51, G54, N55 |
| CDR-H3 (FIG. 2A) | D99, I100, F105, D106 | Y102, G103 |
| CDR-L1 (FIG. 2B) | | L27, N33 |
| CDR-L2 (FIG. 2B) | | G49, Q50, N52 |
| CDR-L3 (FIG. 2B) | | N95, V97 |

B. Design and Construction of NNK Libraries

Based on the result of paratope mapping, totally 28 residues were selected for antibody optimization as shown in Table 2. Residue designations for the heavy chain in Tables 2, 3, and 4 correspond to the m909 sequence in FIG. 2A (SEQ ID NO. 24) and residues for the light chain correspond to the m909 sequence in FIG. 2B (SEQ ID NO. 25). Mutants were expressed in *E. coli* in 96-well plates. The crude protein secreted in medium was analyzed by ELISA for assessment of antigen-antibody binding affinity. The "beneficial mutants" that increased antibody affinity were confirmed by affinity ranking. Clones with improved dissociation rates were selected for sequencing.

TABLE 2

Residues selected for NNK Library Screening

| No. | VL Region | No. | VH Region |
|---|---|---|---|
| 1 | N51 | 16 | G26 |
| 2 | R53 | 17 | T28 |
| 3 | P54 | 18 | S31 |
| 4 | S55 | 19 | M34 |
| 5 | D88 | 20 | W50 |
| 6 | S89 | 21 | A53 |
| 7 | R90 | 22 | G56 |
| 8 | V91 | 23 | N57 |
| 9 | S92 | 24 | S101 |
| 10 | T93 | 25 | Y102 |
| 11 | G94 | 26 | G103 |
| 12 | N95 | 27 | S104 |
| 13 | H96 | 28 | Y107 |
| 14 | V97 | | |
| 15 | V98 | | |

TABLE 3

Beneficial mutants identified by NNK library screening

| Region | Mutation |
|---|---|
| VL | N51F |
| VL | R53L |
| VL | N95I |
| VH | S31Y, S31I |
| VH | N57F |

C. Design and Construction of Combinatorial Library

Once the "beneficial mutants" were identified, a combinatorial library was constructed with random combinations of these mutations. Hundreds of clones were randomly selected and analyzed by ELISA. The top combinations of "beneficial mutants" that resulted in highest antibody affinity increases were finally selected for affinity ranking. Clones with improved dissociation rates were sequenced.

TABLE 4

Affinity matured antibodies identified by combinatorial library screening

| Clone Identifier | VL | | | | VH | |
|---|---|---|---|---|---|---|
| A | N51F | R53L | N95I | | S31Y | N57F |
| B | N51F | R53L | N95I | A16V | S31Y | N57F |
| C | N51F | | N95I | | S31Y | N57F |
| D | N51F | R53L | N95I | | S31Y | |
| E (ASO4498) | N51F | | N95I | | S31Y | |
| F | N51F | R53L | | | S31Y | |
| G | N51F | R53L | N95I | | S31I | |
| H | N51F | | N95I | | S31I | |
| I | | R53L | N95I | | S31I | |
| J | | | N95I | | S31Y | N57F |
| K | | | N95I | | S31Y | |
| L | N51F | | | | S31I | |
| M | N51F | R53L | | | S31I | |
| N | | | N95I | | S31Y | |
| 0 | | R53L | | | S31Y | |
| P | | | | | S31I | N57F |

D. ELISA

Microtiter ELISA plates were coated with 1 μg/ml antigen protein in 100 μl coating buffer at 4° C. overnight, and subsequently incubated with blocking buffer at 37° C. for 2 hours. Then the plates were washed with washing buffer and incubated with 100 μl antibody-containing supernatants at 37° C. for 1.5 hours. Next the plates were washed with washing buffer and incubated with 100 μl secondary antibody (0.1 μg/ml goat antihuman IgG [HRP]) for 45 minutes. After washing, the reaction was developed with 100 μTMB substrate for 10 minutes at room temperature and stopped by adding 100 μl of 1 M HCl. The absorbance values were measured at 450 nm using a spectrometer.

E. IgG Construction, Expression and Purification

The variable domains of heavy chain (VH) and light chain (VL) encoding the M909 and its affinity-matured antibody were synthesized and inserted into pTT5 vector to construct full length IgG expressing vectors, respectively. The heavy and light chain expressing plasmids were used to co-transfect CHO cells. The recombinant IgGs secreted to the medium were purified using protein A affinity chromatography. Finally, the concentration and purity of proteins were assessed by OD280 and SDS-PAGE, respectively.

Example 3

Binding Characterization of One Representative Antibody

To begin the analysis of the affinity matured antibodies, AS04498 was selected for further analysis. Antibody affinity to antigen protein was determined using a Surface Plasmon Resonance (SPR) biosensor, Biacore T200 (GE Healthcare). Antibody was immobilized on the sensor chip through Fc capture method. Antigen protein was used as the analyte. The data of dissociation (kd) and association (k0) rate constants were obtained using Biacore T200 evaluation software. The equilibrium dissociation constants (KD) were calculated from the ratio of kd over k0.

FIG. 6A is a line graph displaying the binding properties of chimeric IgG to FRβ at various concentrations of 3.125 nM, 6.25 nM, 12.5 nM, 25 nM, 50 nM, 100 nM, 200 nM, 400 nM.

Figure 6B:
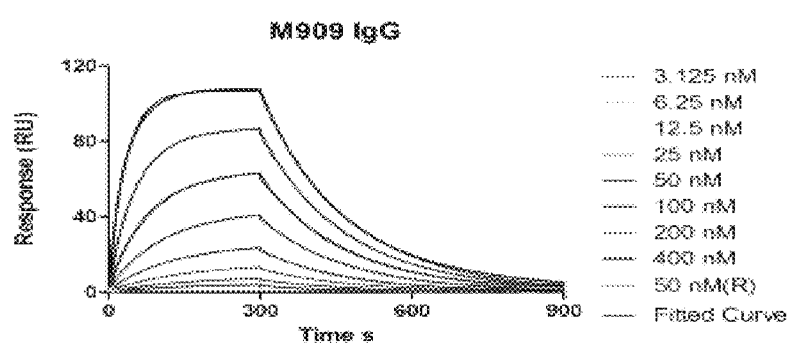
FIG. 6B is a line graph displaying the binding properties of m909 to FRβ at various concentrations of 3.125 nM, 6.25 nM, 12.5 nM, 25 nM, 50 nM, 100 nM, 200 nM, 400 nM.

FIG. 6B is a line graph displaying the binding properties of m909 to FRβ at various concentrations of 3.125 nM, 6.25 nM, 12.5 nM, 25 nM, 50 nM, 100 nM, 200 nM, 400 nM.

Figure 6C:
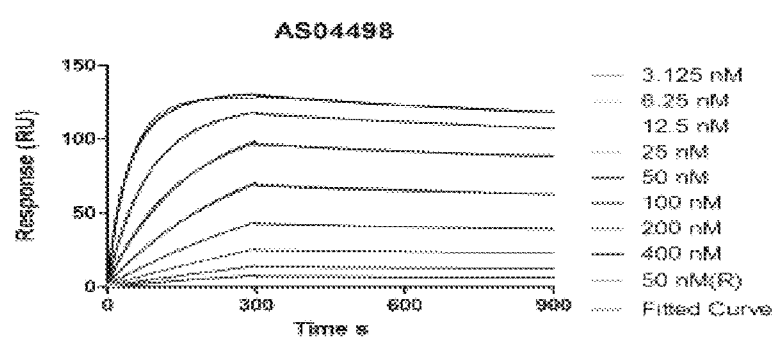
FIG. 6C is a line graph displaying the binding properties of AS04498 to FRβ at various concentrations of 3.125 nM, 6.25 nM, 12.5 nM, 25 nM, 50 nM (X2), 100 nM, 200 nM, 400 nM.

FIG. 6C is a line graph displaying the binding properties of AS04498 to FRβ at various concentrations of 3.125 nM, 6.25 nM, 12.5 nM, 25 nM, 50 nM (X2), 100 nM, 200 nM, 400 nM.

TABLE 5 provides a summary of the binding data displayed in FIGS. 6A-6C.

| Ligand | Analyte | $k_a$(1/Ms) | $K_d$ (1/s) | $K_D$(M) | Rmax (RU) | $Chi^2$ ($RU^2$) | Fold Increase |
|---|---|---|---|---|---|---|---|
| Chimeric IgG | hFRβ | 6.35E+04 | 0.005986 | 9.43E−08 | 121.3 | 0.263 | 1 |
| M909 IgG | hFRβ | 6.41E+04 | 0.005916 | 9.24E−08 | 129.8 | 0.284 | NA |
| ASO4498 | hFRβ | 5.77E+04 | 1.44E+04 | 2.50E−09 | 129.4 | 0.336 | 38 |

As shown in FIGS. 6A-6C and summarized in Table 5, the equilibrium dissociation constant ($K_D$) of AS04498 antibody was at 2.5 nM, 38 times higher than the chimeric IgG control. In this particular experiment, the equilibrium dissociation constant ($K_D$) of m909 was 92 nM.

The smaller the dissociation constant, the more tightly bound the ligand is, or the higher the affinity between antibody and receptor. For example, an antibody with a nanomolar (nM) dissociation constant binds more tightly to a particular receptor than an antibody with a micromolar (μM) dissociation constant.

Example 4

Therapeutic Efficacy of One Representative Antibody

Affinity matured antibody AS04498 binds with higher affinity to FRβ compared to m909. We investigated the efficacy of AS04498 in tumor control as compared to m909.

Materials and Methods

NCr nude mice (athymic nude) were purchased from Taconic BioSciences, Inc (Hudson, N.Y.). Mice were fed Teklad irradiated (sterilized) mouse diet and bedded with Teklad irradiated (sterilized) corncob bedding from Envigo (Indianapolis, Ind.). Mice were housed in Optimice carousel sterile quarters with filtered air supply in disposable cages from Animal Care Systems, Inc. (Centennial, Colo.).

Cells, $5\times10^6$ MV 411 cells in Matrigel, were subcutaneously injected into the left hind flank of 5-6 week-old athymic nude mice. The study began when tumors reached a mean volume of 192 $mm^3$.

Intraperitoneal dosing occurred on Monday, Wednesday, and Friday with 1004, of study agent or control. The treatment vehicle was PBS. Dosing continued for 3 weeks, followed by a three-day observation period. Tumor volume was measured $[(L\times W^2)/2]$ by caliper twice per week.

Weight measurements were taken during tumor measurement. Mortality/morbidity was observed and recorded throughout the study. The mice were sacrificed by $CO_2$ asphyxiation followed by cervical dislocation at end of study (animals were sacrificed before study completion if tumors reached >3,000 $mm^3$).

Results

Figure 7:
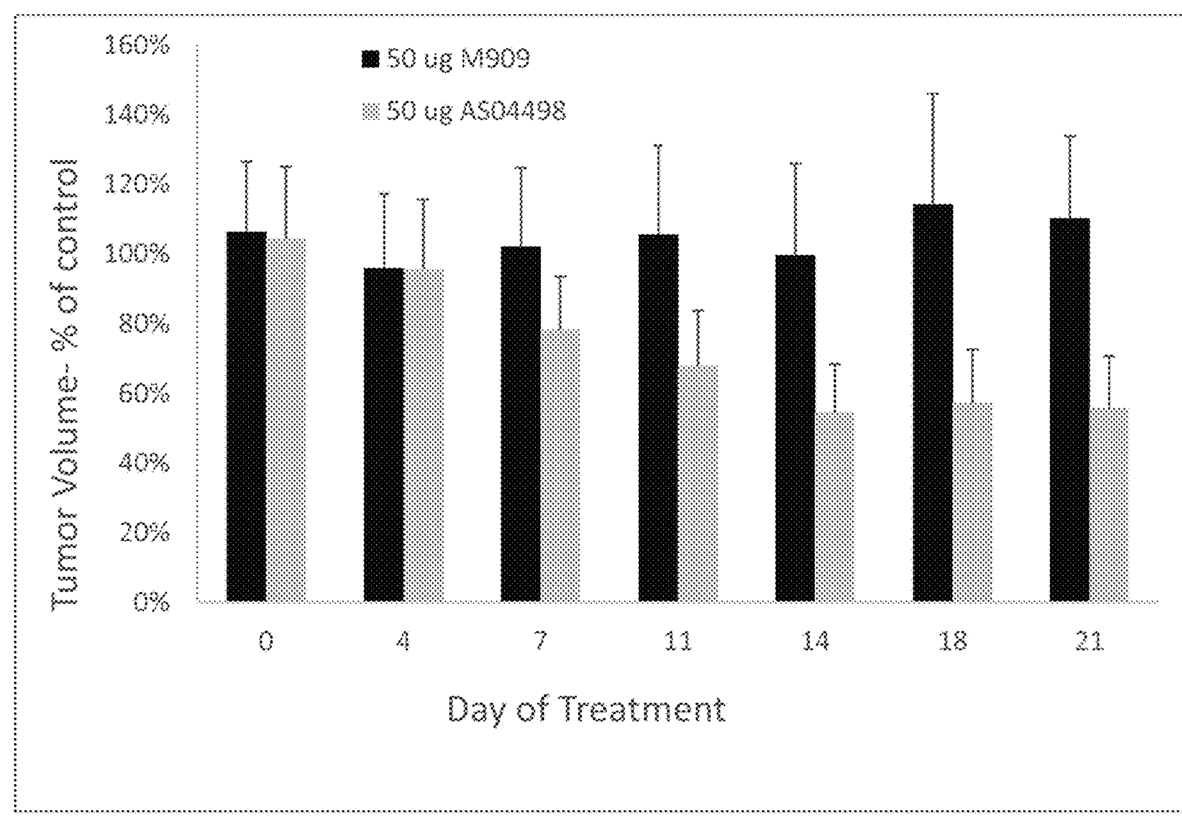
FIG. 7 is a bar graph displaying the volume of a tumor in mice in relation to the administration of the monoclonal antibody m909 or the affinity matured ("AM") AS04498 antibody. Both m909 and AS04498 bind FRβ.

No adverse events were noted throughout the course of the study. As depicted in FIG. 7, administration of 50 μg is AS04498 had the greatest anti-tumor effect, which reduced the volume roughly in half. AS04498 significantly reduced tumor growth in comparison to m909, and functioned as an effective therapeutic.

Example 5

Antibody Affinity Assay

An antibody affinity assay was performed to compare AS04498 to the m909 antibody. Human monocytic leukaemia cell line, THP-1, which was FR-β positive, was used to determine the dissociation of the antibody from FR-β expressing cells.

Material and Methods

Cells (100,000 cells) were stained with m909-biotinylated, 2 μl (1 μg/ml), AS04498-biotinylated, 2 μl (1 μg/ml), human IgG Isotype, 2 μl (1 μg/ml) for 1 hour at 4° C. Cells were washed twice with FACS buffer by adding 500 μl of FACS buffer and spinning down cells at 1200 rpm for 5 min.

Non-biotinylated antibodies (m909, AS04498) were added to respective wells (2 μl (1 μg/ml)) and incubated at 4° C. and 37° C. for different time points (0 hour, 2 hour, and 4 hour). Samples were washed at their respective time points and stained with SA APC for 20 minutes. Samples were washed and analyzed by flow cytometry.

Results

Figure 8A:
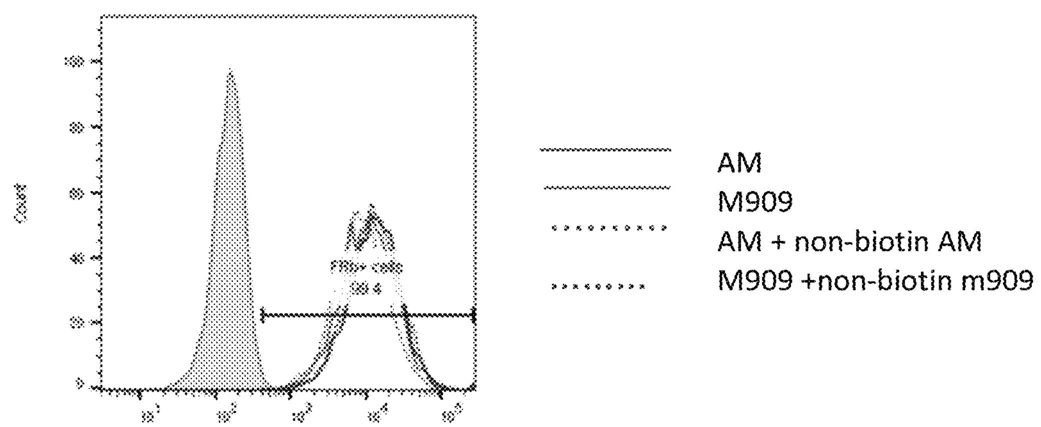
FIG. 8A is a flow cytometry graph of THP-1 cells, which express FRβ, displaying binding properties of the m909 antibody and the AS04498 antibody at 4° C. at 0 hours.
Figure 8B:
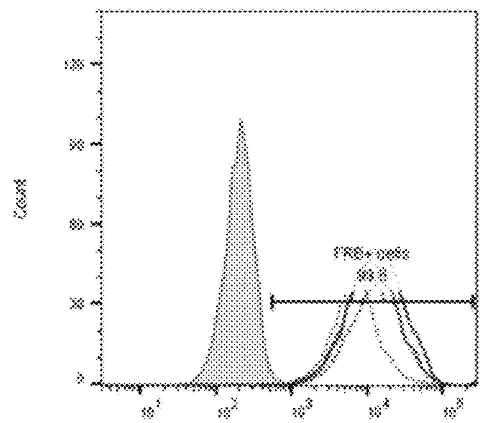
FIG. 8B is a flow cytometry graph of THP-1 cells, which express FRβ, displaying binding properties of the m909 antibody and the AS04498 antibody at 4° C. at 2 hours.
Figure 8C:
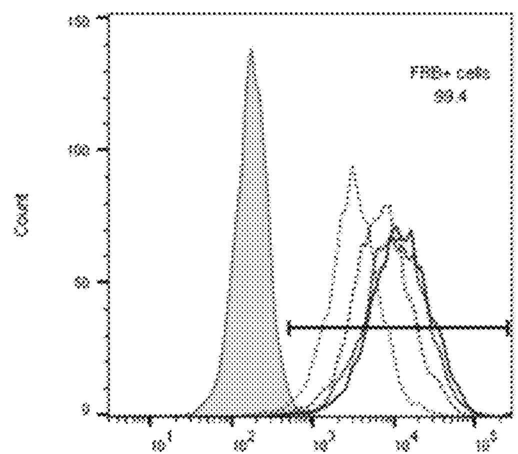
FIG. 8C is a flow cytometry graph of THP-1 cells, which express FRβ, displaying binding properties of the m909 antibody and the AS04498 antibody at 4° C. at 4 hours.

Flow cytometry graphs for binding of m909 antibody and AS04498 are shown in FIGS. 8 and 9. FIG. 8A shows the binding of m909 antibody and AS04498 at 4° C. at 0 hour. FIG. 8B shows the binding of m909 antibody and AS04498 at 4° C. at 2 hour time point. FIG. 8C shows the binding of m909 antibody and AS04498 at 4° C. at 4 hour time point.

Figure 9A:
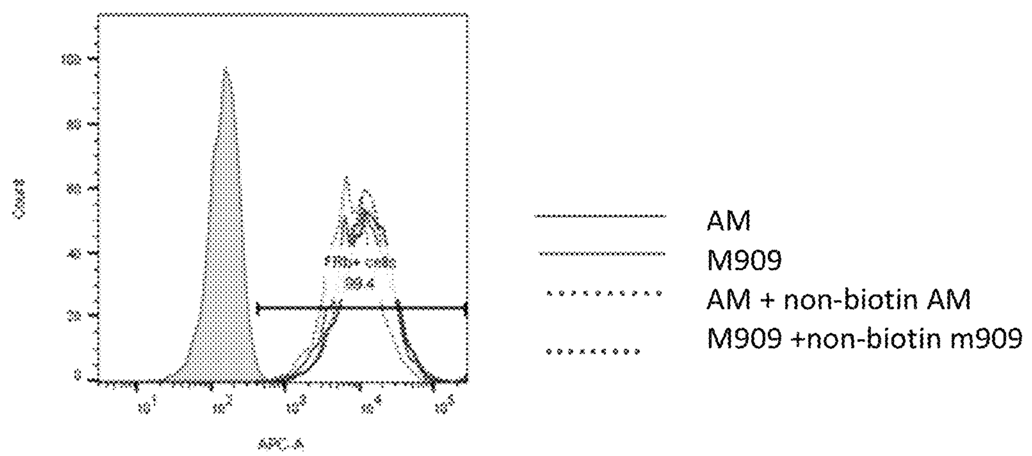
FIG. 9A is a flow cytometry graph of THP-1 cells, which express FRβ, displaying binding properties of the m909 antibody and the AS04498 antibody at 37° C. at 0 hours.
Figure 9B:
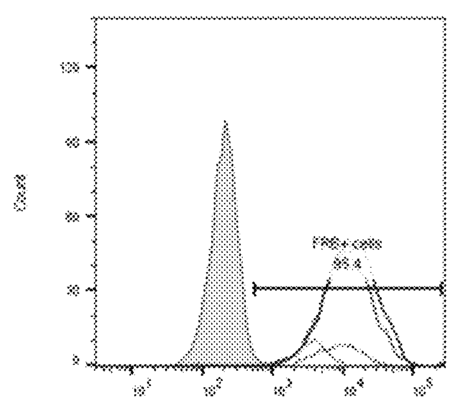
FIG. 9B is a flow cytometry graph of THP-1 cells, which express FRβ, displaying binding properties of the m909 antibody and the AS04498 antibody at 37° C. at 2 hours.
Figure 9C:
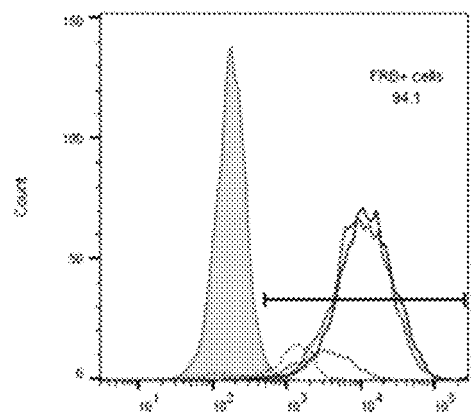
FIG. 9C is a flow cytometry graph of THP-1 cells, which express FRβ, displaying binding properties of the m909 antibody and the AS04498 antibody at 37° C. at 4 hours.
Figure 10:
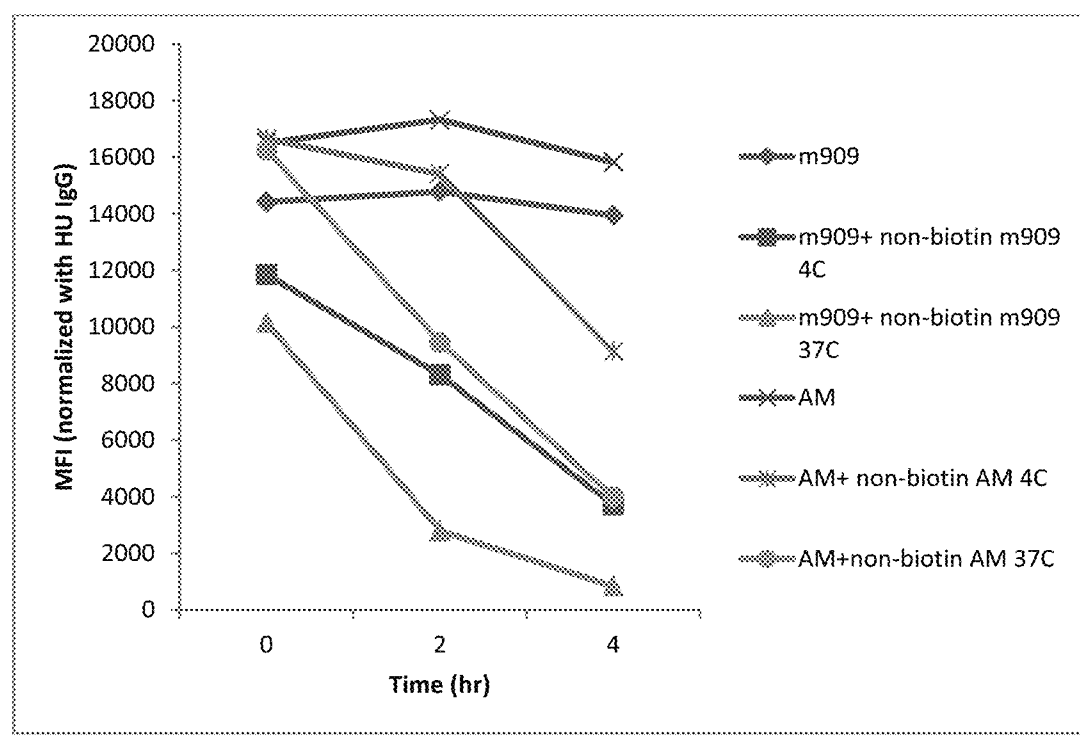
FIG. 10 is a bar graph displaying the binding affinity of the m909 antibody and the AS04498 antibody in THP-1 cells expressing FRβ.

FIG. 9A shows the binding of m909 antibody and AS04498 at 37° C. at 0 hour. FIG. 9B shows the binding of m909 antibody and AS04498 at 37° C. at 2 hour time point. FIG. 9C shows the binding of m909 antibody and AS04498 at 37° C. at 4 hour time point FIG. 10 is a bar graph depicting the binding of the m909 antibody and the AS04498 antibody. At each time point measured, AS04498 has increased binding as comparted to m909. AS04498 has previously been shown to have a higher binding affinity as compared to m909. The data indicates that AS04498 may remain bound for longer periods of time to FRβ as compared to the m909 antibody.

At the 2 hour time point, ASO4498 has increased binding as compared to the m909 antibody. This indicates that AS0449 may have a slower off rate than m909.

Example 6

MV-411 Xenograft Model

We compared the m909 antibody and the AS04498 antibody in a mouse xenograft model.

Material and Methods

MV-411 cells in Matrigel ($5\times10^6$) were injected subcutaneously into left hind flank of 5-6 week old athymic nude mice on Day 0. There were eight mice per group.

Dosing was initiated (day 0) when tumors reached a mean volume of 250 $mm^3$. Study agent (100 μL) or vehicle (PBS) was administered intraperitoneal (IP) on Monday, Wednesday, and Friday for 3 weeks. After dosing ended, mice were observed for an additional 3 weeks. Tumor volume [$(L\times W^2)/2$] was measured by caliper twice per week.

Results

Figure 11:
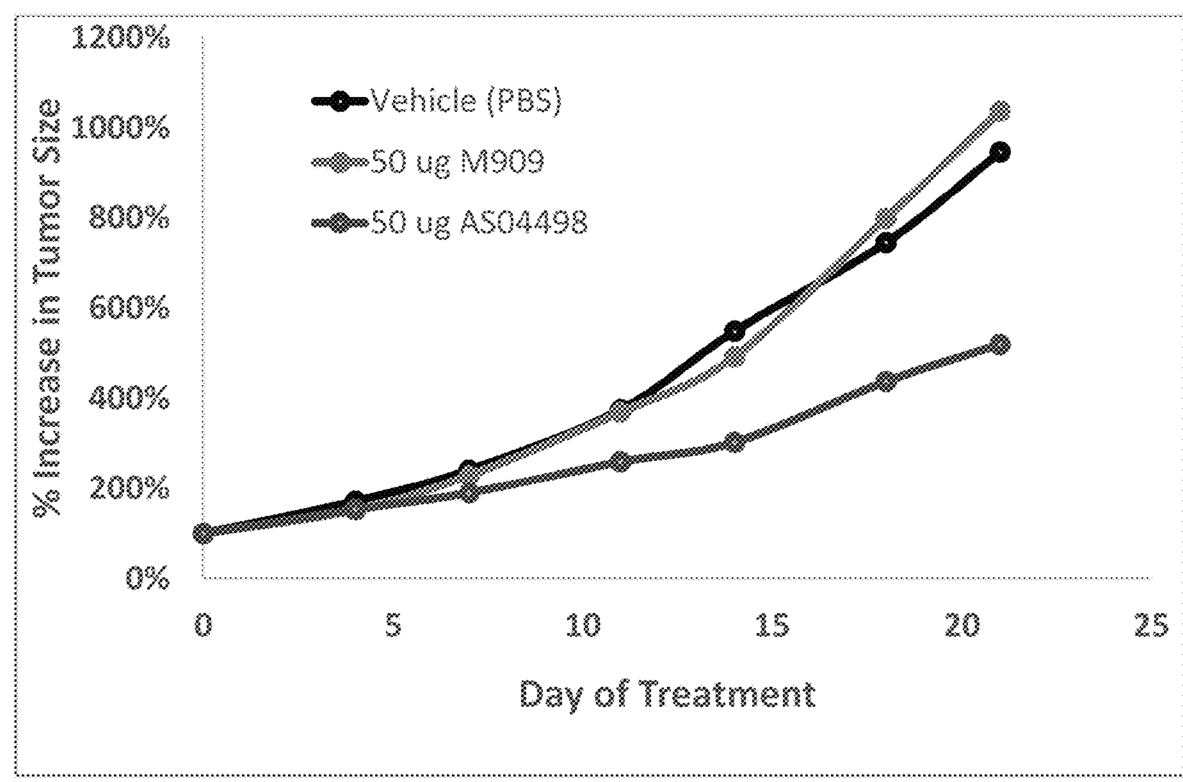
FIG. 11 is a bar graph displaying the efficacy of anti-FRβ antibodies in the MV-411 xenograft AML Model.

As depicted in FIG. 11, AS04498 inhibited tumor growth more effectively than the m909 antibody. AS04498 performed more effectively at multiple time points, and the disparity in effectiveness of the two antibodies increased with increasing time periods. Not to be bound by any particular theory, AS04498 has a higher affinity for FR-β, and increased therapeutic efficacy.

Example 7

Apoptosis Assay

Materials and Methods

CHOb and CHO-K1 cells were plated at $0.3^6$ cells/ml in a 12 well plate. The plates were incubated at 37° C. incubator for 24 hours. Cells were harvested and dead cells floating in the supernatant were collected.

Cells were stained by adding Annexin-V antibody in Annexin V binding buffer and 7-AAD stain at the same time. An aliquot of CHOb and CHO-K1 cells were incubated at 0 and 10 μg/ml of AS04498 (AM), and 10 μg/ml m909 to examine FRβ expression.

After incubation at 4° C., samples were analyzed on Fortessa flow cytometry machine.

Results 10,000 events were collected. Apoptotic events were analyzed at a 12 hour time point. As shown in Table 6, higher early apoptotic FRβ+ cells with m909. Conversely, as shown in Table 7, there were higher late apoptotic total cells with m909

TABLE 6

Apoptotic events in FR-β Positive Cells

| FR-β+ cells | Necrotic q1 | Late Apoptosis q2 | Early Apoptosis q3 | Live cells q4 |
|---|---|---|---|---|
| CHOb0 | 15.6% | 75.6% | 5.56% | 3.31% |
| CHOb m909 10 | 10.3% | 63.0% | 17.1% | 9.60% |
| CHOb_m909_APC_10 | 10.5% | 57.7% | 20.4% | 11.5% |
| CHOb AM 10 | 16.1% | 77.0% | 4.01% | 2.94% |
| CHOb_Am_APC_10 | 17.0% | 77.1% | 3.76% | 2.18% |

TABLE 7

Apoptotic Events in Total Cells

| Total Cells | Necrotic q1 | Late Apoptosis q2 | Early Apoptosis q3 | Live cells q4 |
|---|---|---|---|---|
| CHOb HUIgG 0 | 1.26% | 23.4% | 62.1% | 13.2% |
| CHOb0 | 1.26% | 25.8% | 60.3% | 12.7% |
| CHOb m909 10 | 2.08% | 42.1% | 45.8% | 10.1% |
| CHOb_m909_APC_10 | 2.42% | 47.5% | 40.2% | 9.92% |
| CHOb AM 10 | 1.43% | 25.5% | 60.4% | 12.7% |
| CHOb_Am_APC_10 | 2.07% | 27.7% | 57.8% | 12.4% |

Example 8

Mouse Tumor and Blood Analysis

We investigated the ability of FRβ to bind and deplete macrophages in mouse blood and tumor samples.

Materials and Methods

THP-1 cells were administered intravenously on day 0. Dosing was initiated on day 2. Mice were dosed by the IP route MWF for a total of 10 doses. On day 42, tumors were removed from the mice and digested with GentleMACs.

Blood was collected using cardiac puncture. Cells were isolated and stained for analysis by flow cytometry.

Results

Figure 12A:
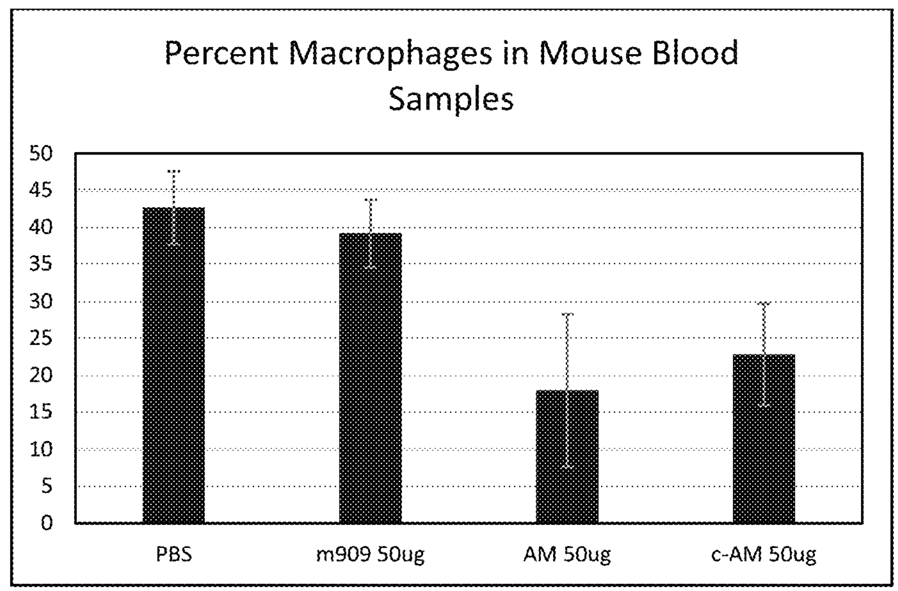
FIG. 12A is a bar graph displaying depletion of mouse macrophages in blood samples using the M909 antibody and the AS04498 antibody.

The percentage of macrophages in the mouse blood and tumor samples was determined by the percentage of mCD11b and F4-80 double positive cells (see Table 8 for markers). As shown in FIG. 12A, AS04498 effectively depleted or reduced the number of macrophages in the mouse blood sample. AS04498 performed better than the m909 antibody.

Figure 12B:
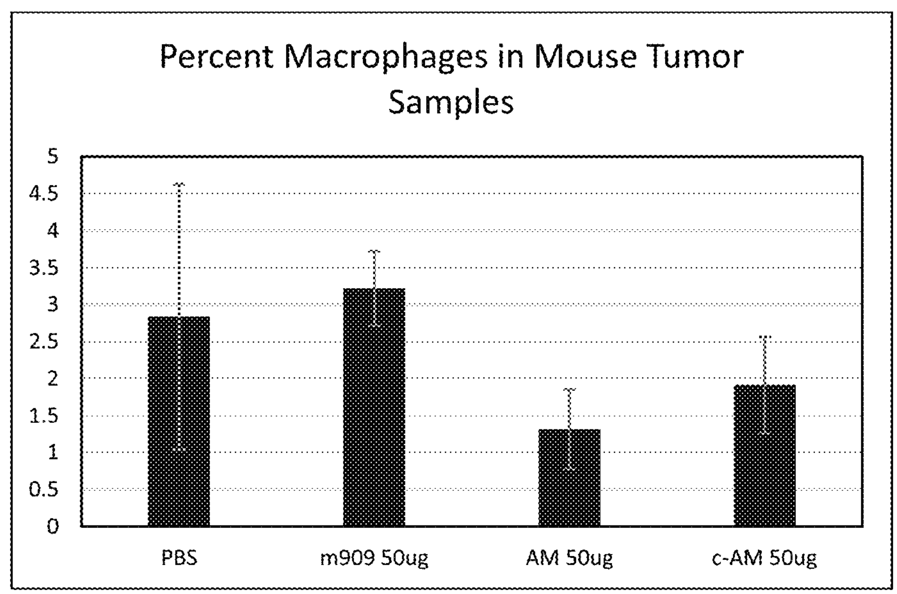
FIG. 12B is a bar graph displaying depletion of mouse macrophages in tumor samples using the M909 antibody and the AS04498 antibody.

As shown in FIG. 12B, AS04498 effectively depleted or reduced the number of macrophages in the mouse tumor sample. AS04498 performed better than the m909 antibody.

TABLE 8

| Markers used to identify macrophages | |
|---|---|
| Marker | Recognize |
| CD33_PE | Transmembrane receptor expressed on myeloid lineage cells |
| M909_-Biotin, SA-APC | FRβ positive cells |
| F4/80_PE-Cy7 | Mouse macrophage marker |
| mCD11b-Pacific Blue | Mouse macrophage marker |
| Aqua Live Dead | Live/dead cells |
| GFP | THP-1 cells engineered to express GFP-Luc - tumor marker |

Example 9

Humanized Thioglycollate Inflammation Model

Materials and Methods

Hu-CD34 NSG™ mice that were engrafted with human CD34+ cells with >25% human CD45+ cells in the peripheral blood were used for the study. Mice were at least 12 weeks post engraftment. Attempts were made to distribute donors equally into groups of 5.

The mice were injected IP with 4% thioglycolate on Day 0 and dosed with 1 μg or 5 μg of m909 or AS04498 antibody on Day 2.

All animals were euthanized by $CO_2$ asphyxiation on Day 4 and cells were collected via peritoneal lavage. Samples were analyzed for the following markers: hCD45, CD68, CD14, anti-FRb, and viability dye (7AAD). Counting beads were included in each sample for absolute cell number determinations.

Results

Figure 13:
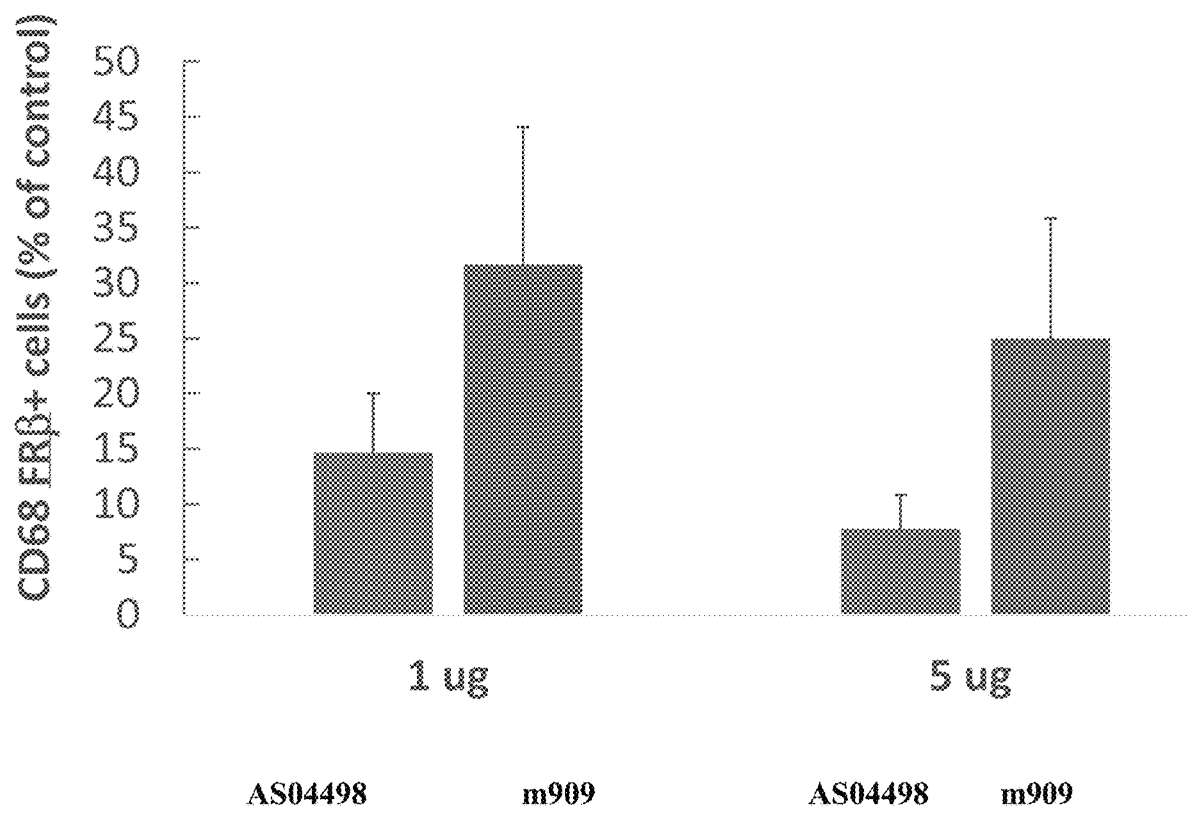
FIG. 13 is a bar graph displaying the inhibition of CD68+, FRβ+ cells using m909 and AS04498 with the data presented as % control.

As shown in FIG. 13, AS04498 effectively inhibited cells positive for both CD68, and FRβ. ASO4498 was more effective than m909 in inhibiting cells positive for both CD68 and FRβ positive cells. AS04498 was effective at both 1 μg and 5 μg doses.

Figure 14:
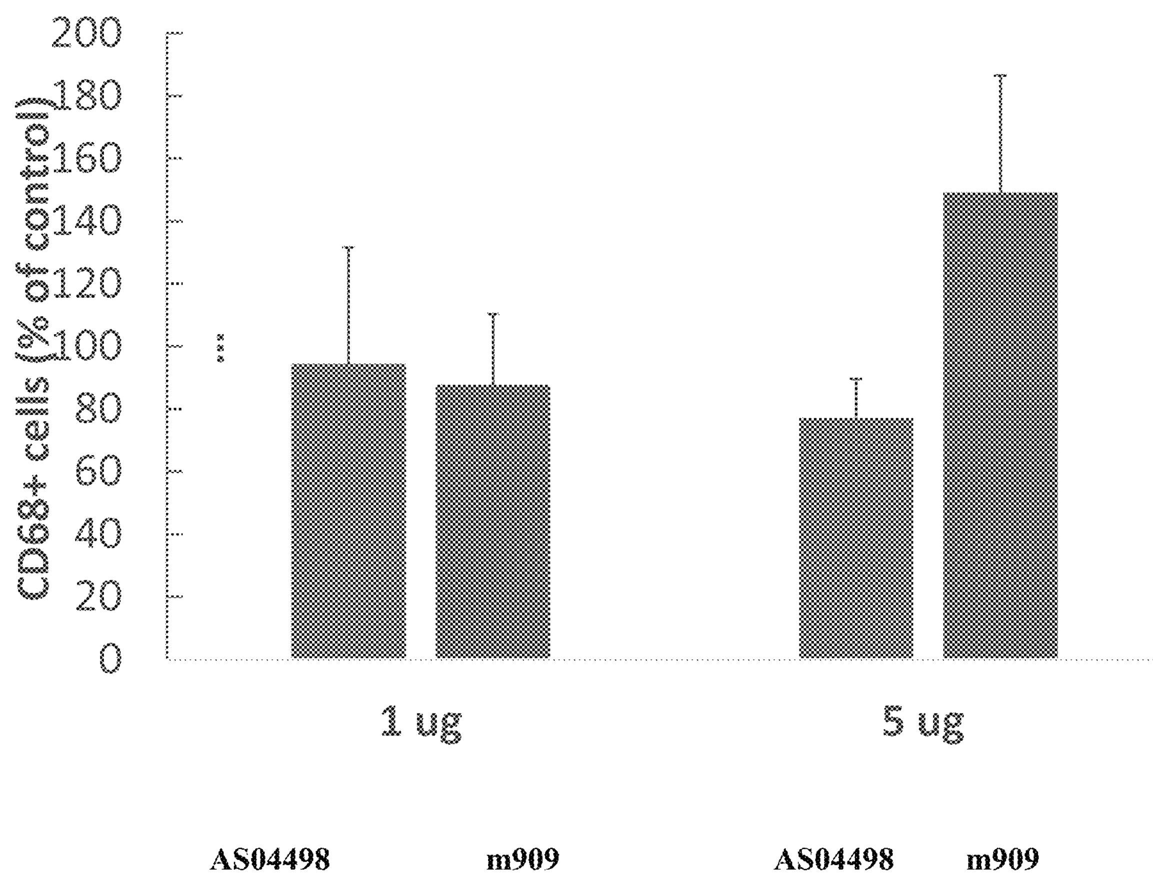
FIG. 14 is a bar graph displaying the inhibition of CD68+ cells using m909 and AS04498 with the data presented as % control.

As shown in FIG. 14, AS04498 effectively inhibited CD68 positive cells. In this case, AS04498 was more effective at the 5 μg dose.

Figure 15:
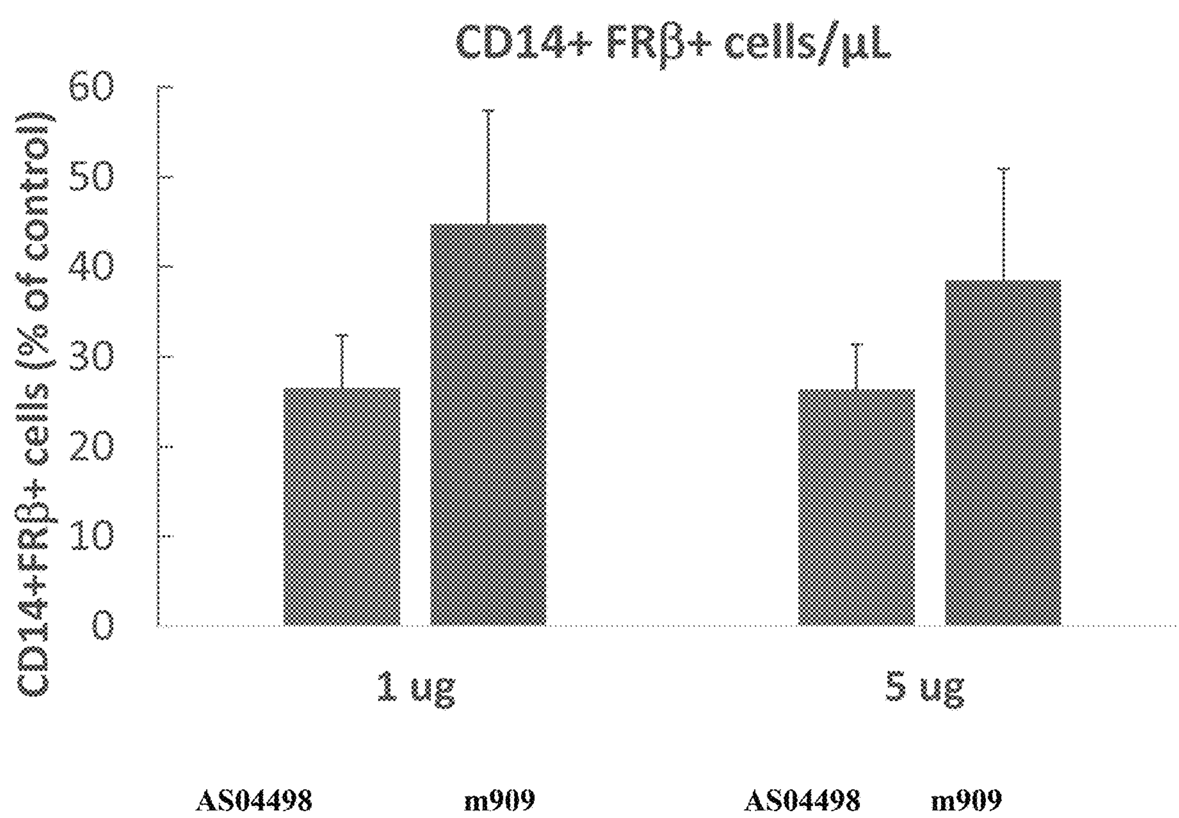
FIG. 15 is a bar graph displaying the inhibition of CD14+, FRβ+ cells using m909 and AS04498 with the data presented as % control.

As shown in FIG. 15, AS04498 effectively inhibited cells positive for both CD14 and FRβ. AS04498 was more effective than m909 in inhibiting cells positive for both CD14, and FRβ. AS04498 was effective at both 1 μg and 5 μg doses.

Figure 16:
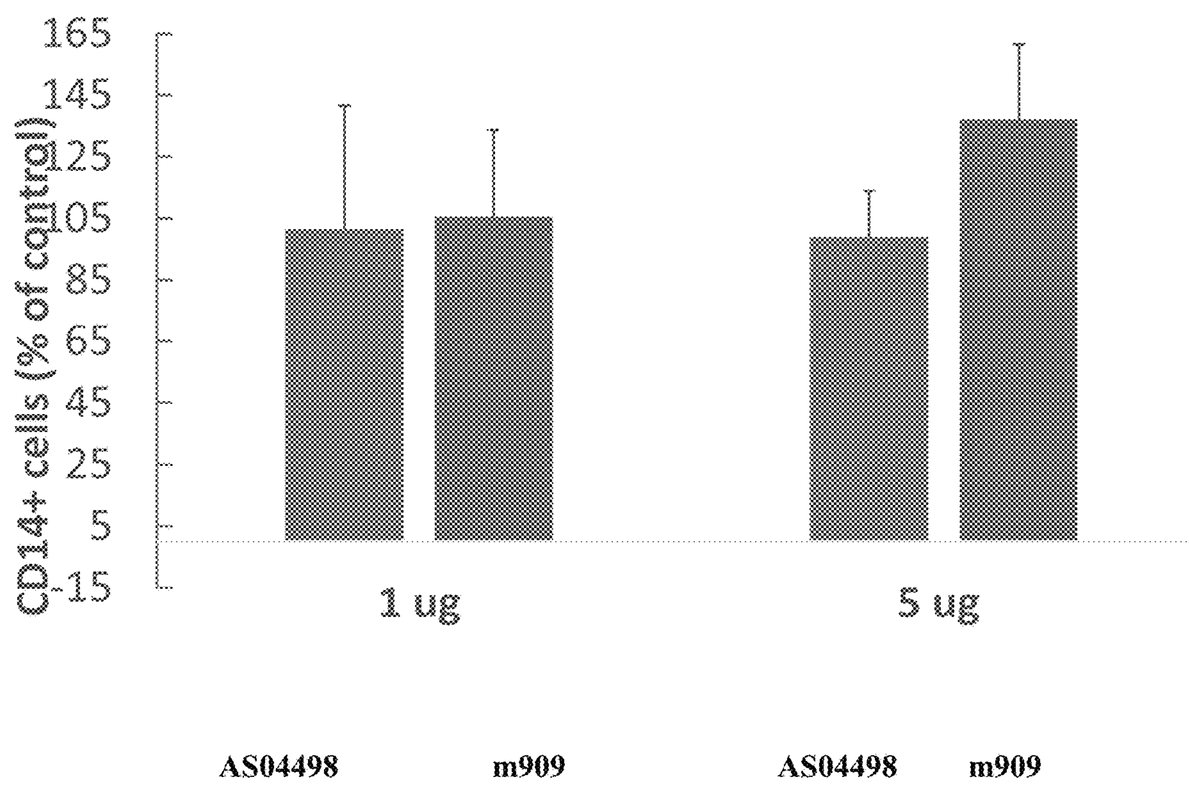
FIG. 16 is a bar graph displaying the inhibition of CD14+ cells using m909 and AS04498 with the data presented as % control.

As shown in FIG. 16, AS04498 effectively inhibited cells positive for CD14. ASO4498 was more effective than m909 in inhibiting cells positive for CD14. AS04498 was more effective at the 5 μg dose.

Figure 17:
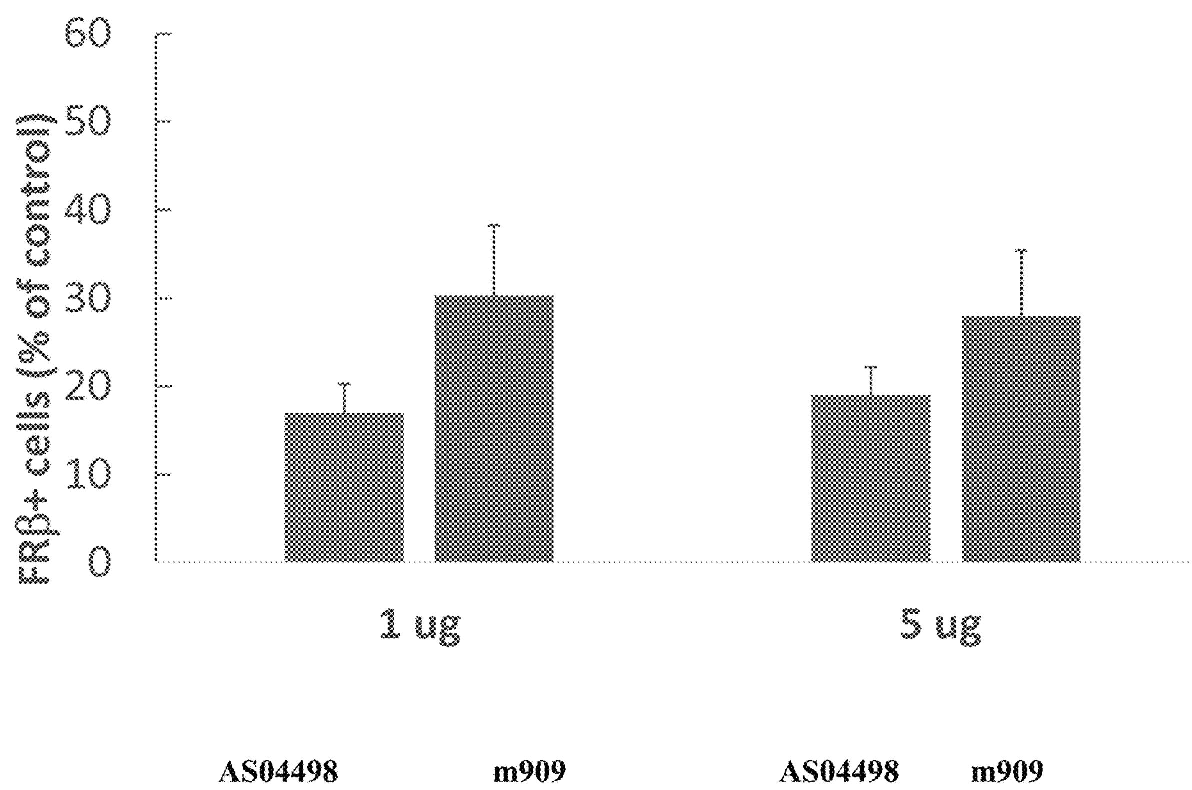
FIG. 17 is a bar graph displaying the inhibition FRβ+ cells using m909 and AS04498 with the data presented as % control.

As shown in FIG. 17, AS04498 effectively inhibited cells positive for FRβ. ASO4498 was more effective than m909 in inhibiting cells positive for FRβ.

It is to be understood that while the antibodies, fragments thereof, compounds, and methods have been described in conjunction with the detailed description thereof, the foregoing description is intended to illustrate and not limit the scope of the disclosure, which is defined by the scope of the appended claims. Other aspects, advantages, and modifications are within the scope of the following claims.

INFORMAL SEQUENCE LISTING

```
SEQ ID NO. 1 (S31Y
TYPE: PRT
ORGANISM: ARTIFICIAL SEQUENCE
OTHER INFORMATION: HEAVY CHAIN COMPLEMENTARY DETERMINING
REGION FROM A HUMAN ANTI-HUMAN FR BETA ANTIBODY
SEQUENCE 1
GLY TYR THR PHE THR TYR TYR ALA

SEQ ID NO. 2
TYPE: PRT
ORGANISM: ARTIFICIAL SEQUENCE
OTHER INFORMATION: HEAVY CHAIN COMPLEMENTARY DETERMINING
REGION FROM A HUMAN ANTI-HUMAN FR BETA ANTIBODY
SEQUENCE 2
LYS TYR SER GLN LYS PHE GLN

SEQ ID NO. 3
TYPE: PRT
ORGANISM: ARTIFICIAL SEQUENCE
OTHER INFORMATION: HEAVY CHAIN COMPLEMENTARY DETERMINING
REGION FROM A HUMAN ANTI-HUMAN FR BETA ANTIBODY
SEQUENCE 3
ALA ARG ASP ILE SER TYR GLY SER PHE ASP TYR TRP

SEQ ID NO. 4
TYPE: PRT
ORGANISM: ARTIFICIAL SEQUENCE
OTHER INFORMATION: LIGHT CHAIN COMPLEMENTARY DETERMINING REGION
FROM A HUMAN ANTI-HUMAN FR BETA ANTIBODY
SEQUENCE 4
SER LEU ARG SER ASN TYR

SEQ ID NO. 5
TYPE: PRT
ORGANISM: ARTIFICIAL SEQUENCE
OTHER INFORMATION: LIGHT CHAIN COMPLEMENTARY DETERMINING REGION
FROM A HUMAN ANTI-HUMAN FR BETA ANTIBODY
SEQUENCE 5 (N51F)
GLY GLN PHE
```

-continued

INFORMAL SEQUENCE LISTING

SEQ ID NO. 6
TYPE: PRT
ORGANISM: ARTIFICIAL SEQUENCE
OTHER INFORMATION: LIGHT CHAIN COMPLEMENTARY DETERMINING REGION FROM A HUMAN ANTI-HUMAN FR BETA ANTIBODY
SEQUENCE 6 (N95I)
ASP SER ARG VAL SER THR GLY ILE HIS VAL VAL PHE

SEQ ID NO. 7
TYPE: PRT
ORGANISM: ARTIFICIAL SEQUENCE
OTHER INFORMATION: HEAVY CHAIN SEQUENCE FROM A HUMAN ANTI-HUMAN FR BETA ANTIBODY
SEQUENCE 7 (S31Y)
EVQLVQSGAEVKKPGASVKVSCKASGYTFTYYAMHWVRQAPGQRLEWMGWINAGNG
NTKYSQKFQGRVTITRDTSASTAYMELSSLRSEDTAVYYCARDISYGSFDYWGQGTLVT
VSS

SEQ ID NO. 8
TYPE: PRT
ORGANISM: ARTIFICIAL SEQUENCE
OTHER INFORMATION: HEAVY CHAIN SEQUENCE FROM A HUMAN ANTI-HUMAN FR BETA ANTIBODY
SEQ ID NO. 8 (S31Y)
EVQLVQSGAEVKKPGASVKVSCKASGYTFTYYAMHWVRQAPGQRLEWMGWINAGNG
NTKYSQKFQGRVTITRDTSASTAYMELSSLRSEDTAVYYCARDISYGSFDYWGQGTLVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPP

SEQ ID NO. 9
TYPE: PRT
ORGANISM: ARTIFICIAL SEQUENCE
OTHER INFORMATION: HEAVY CHAIN SEQUENCE FROM A HUMAN ANTI-HUMAN FR BETA ANTIBODY
SEQ ID NO. 9 (S31Y)
MGWSWILLFLLSVTAGVHSEVQLVQSGAEVKKPGASVKVSCKASGYTFTYYAMHWVR
QAPGQRLEWMGWINAGNGNTKYSQKFQGRVTITRDTSASTAYMELSSLRSEDTAVYYC
ARDISYGSFDYWGQGTLVTVSS*ASTKGPSVFPLAPSSKSTSGGTAALGCLVKDYFPEPVTVS*
*WNSGALTSGVHTFPAVLQSSGLYSLSSVVTVPSSSLGTQTYICNVNHKPSNTKVDKKVEPKSCD*
*KTHTCPPCPAPELLGGPSVFLFPPKPKDTLMISRTPEVTCVVVDVSHEDPEVKFNWYVDGVE*
*VHNAKTKPREEQYNSTYRVVSVLTVLHQDWLNGKEYKCKVSNKALPAPIEKTISKAKGQPREP*
*QVYTLPPSRDELTKNQVSLTCLVKGFYPSDIAVEWESNGQPENNYKTTPPVLDSDGSFFLYSK*
*LTVDKSRWQQGNVFSCSVMHEALHNHYTQKSLSLSPGK*

SEQ ID NO. 10 (DNA ENCODING SEQ ID NO. 9)
TYPE: DNA
ORGANISM: ARTIFICIAL SEQUENCE
OTHER INFORMATION: NUCLEIC ACID SEQUENCE ENCODING HEAVY CHAIN FROM A HUMAN ANTI-HUMAN FR BETA ANTIBODY
SEQ ID NO. 10 (S31Y)
ATGGGCTGGAGCTGGATCCTGCTGTTCCTCCTGAGCGTGACAGCAGGAGTGCACAGC
GAGGTGCAGCTGGTCCAGTCCGGCGCTGAGGTGAAGAAACCAGGGGCATCCGTGAA
AGTCTCCTGCAAAGCCAGTGGCTACACCTTCACATACTATGCCATGCACTGGGTGAG
GCAGGCTCCAGGACAGCGACTGGAATGGATGGGCTGGATCAACGCCGGCAACGGG
AATACTAAGTACTCCCAGAAATTTCAGGGGCGGGTGACTATTACCAGAGACACCTC
AGCCAGCACAGCTTATATGGAGCTGAGCTCCCTGCGAAGCGAAGATACAGCAGTCT
ACTATTGTGCCAGAGACATTAGTTACGGAAGCTTTGATTATTGGGGACAGGGCACAC
TGGTGACTGTCTCTAGTGCTAGCACCAAGGGCCCATCGGTCTTCCCCCTGGCACCCT
CCTCCAAGAGCACCTCTGGGGGCACAGCGGCCCTGGGCTGCCTGGTCAAGGACTAC
TTCCCCGAACCGGTGACGGTGTCGTGGAACTCAGGCGCCCTGACCAGCGGCGTGCA
CACCTTCCCGGCTGTCCTACAGTCCTCAGGACTCTACTCCCTCAGCAGCGTGGTGAC
CGTGCCCTCCAGCAGCTTGGGCACCCAGACCTACATCTGCAACGTGAATCACAAGCC
CAGCAACACCAAGGTGGACAAGAAAGTTGAGCCCAAATCTTGTGACAAAACTCACA
CATGCCCACCGTGCCCAGCACCTGAACTCCTGGGGGGACCGTCAGTCTTCCTCTTCC
CCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGG
CGTGGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCT
CCAAAGCCAAAGGGCAGCCCCGAGAACCACAGGTGTACACCCTGCCCCCATCCCGG
GATGAGCTGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAAGCTCACCG
TGGACAAGAGCAGGTGGCAGCAGGGGAACGTCTTCTCATGCTCCGTGATGCATGAG
GCTCTGCACAACCACTACACGCAGAAGAGCCTCTCCCTGTCTCCGGGTAAATGA

-continued

INFORMAL SEQUENCE LISTING

SEQ ID NO. 11
TYPE: PRT
ORGANISM: ARTIFICIAL SEQUENCE
OTHER INFORMATION: LIGHT CHAIN SEQUENCE FROM A HUMAN ANTI-HUMAN FR BETA ANTIBODY
SEQUENCE 11
SSELTQDPAVSVALGQTVRITCQGDSLRSNYANWYQQKPGQAPVLVIYGQFNRPSGIPD
RFSGSSSGNTASLTITGAQAADEADYYCDSRVSTGIHVVFGGGTKLTVLG

SEQ ID NO. 12
TYPE: PRT
ORGANISM: ARTIFICIAL SEQUENCE
OTHER INFORMATION: LIGHT CHAIN SEQUENCE FROM A HUMAN ANTI-HUMAN FR BETA ANTIBODY
SEQUENCE 12
SSELTQDPAVSVALGQTVRITCQGDSLRSNYANWYQQKPGQAPVLVIYGQFNRPSGIPD
RFSGSSSGNTASLTITGAQAADEADYYCDSRVSTGIHVVFGGGTKLTVLGQPKAAPSVT
LFPPSSEELQANKATLVCLISDFYPGAVTVAWKADSSPVKAGVETTTPSKQSNNKYAAS
SYLSLTPEQWKSHRSYSCQVTHEGSTVEKTVAPTECS

SEQ ID NO. 13 (DNA ENCODING SEQ ID NO. 12)
TYPE: DNA
ORGANISM: ARTIFICIAL SEQUENCE
OTHER INFORMATION: NUCLEIC ACID SEQUENCE ENCODING LIGHT CHAIN FROM A HUMAN ANTI-HUMAN FR BETA ANTIBODY
SEQUENCE 13
ATGGGCTGGAGCTGGATCCTGCTGTTCCTCCTGAGCGTGACAGCAGGAGTGCACAGC
TCTTCTGAACTTACTCAAGATCCCGCCGTGTCCGTGGCCCTGGGCCAGACCGTGAGG
ATCACCTGCCAGGGCGACTCCCTGAGGTCCAACTACGCCAATTGGTACCAGCAGAA
GCCCGGCCAGGCCCCCGTGCTGGTCATCTACGGCCAGTTCAACAGGCCCTCCGGCAT
CCCCGACCGCTTCTCCGGCTCCTCCTCCGGCAACACCGCCTCCCTGACCATCACCGG
CGCCCAGGCCGCAGACGAGGCCGACTACTACTGCGATTCCAGGGTGTCCACCGGCA
TCCACGTGGTGTTCGGCGGCGGCACCAAGCTGACCGTGCTGGGCCAGCCCAAGGCC
GCCCCCTCCGTGACCCTGTTCCCCCCCTCCTCCGAGGAGCTGCAGGCCAACAAGGCC
ACCCTGGTCTGCCTGATCTCCGACTTCTACCCCGGCGCCGTGACCGTGGCCTGGAAG
GCCGACTCCTCCCCCGTGAAGGCCGGCGTGGAGACAACCACCCCCTCCAAGCAGTC
CAACAACAAATACGCCGCCTCCTCCTACCTGTCCCTGACCCCCGAGCAGTGGAAGTC
CCACAGGTCCTACTCCTGCCAAGTCACCCACGAGGGCTCCACCGTGGAGAAGACCG
TGGCCCCCACCGAGTGCTCCTAG

SEQ ID NO. 14
TYPE: PRT
ORGANISM: ARTIFICIAL SEQUENCE
OTHER INFORMATION: LIGHT CHAIN COMPLEMENTARY DETERMINING REGION FROM A HUMAN ANTI-HUMAN FR BETA ANTIBODY
SEQUENCE 14
GLY GLN ASN

SEQ ID NO. 15 (N 95 I)
TYPE: PRT
ORGANISM: ARTIFICIAL SEQUENCE
OTHER INFORMATION: LIGHT CHAIN SEQUENCE FROM A HUMAN ANTI-HUMAN FR BETA ANTIBODY
SEQUENCE 15
SSELTQDPAVSVALGQTVRITCQGDSLRSNYANWYQQKPGQAPVLVIYGQNNRPSGIPD
RFSGSSSGNTASLTITGAQAADEADYYCDSRVSTGIHVVFGGGTKLTVLG

SEQ ID NO. 16 (N951)
TYPE: PRT
ORGANISM: ARTIFICIAL SEQUENCE
OTHER INFORMATION: LIGHT CHAIN SEQUENCE FROM A HUMAN ANTI-HUMAN FR BETA ANTIBODY
SEQUENCE 16
SSELTQDPAVSVALGQTVRITCQGDSLRSNYANWYQQKPGQAPVLVIYGQNNRPSGIPD
RFSGSSSGNTASLTITGAQAADEADYYCDSRVSTGIHVVFGGGTKLTVLGQPKAAPSVT
LFPPSSEELQANKATLVCLISDFYPGAVTVAWKADSSPVKAGVETTTPSKQSNNKYAAS
SYLSLTPEQWKSHRSYSCQVTHEGSTVEKTVAPTECS

SEQ ID NO. 17
TYPE: PRT
ORGANISM: ARTIFICIAL SEQUENCE
OTHER INFORMATION: HEAVY CHAIN SEQUENCE FROM A HUMAN ANTI-HUMAN FR BETA ANTIBODY

-continued

INFORMAL SEQUENCE LISTING

SEQUENCE 17 (S31Y; N57F)
EVQLVQSGAEVKKPGASVKVSCKASGYTFTYYAMHWVRQAPGQRLEWMGWINAGNG
FTKYSQKFQGRVTITRDTSASTAYMELSSLRSEDTAVYYCARDISYGSFDYWGQGTLVT
VSS

SEQ ID NO. 18
TYPE: PRT
ORGANISM: ARTIFICIAL SEQUENCE
OTHER INFORMATION: HEAVY CHAIN SEQUENCE FROM A HUMAN ANTI-HUMAN FR BETA ANTIBODY
SEQ ID NO. 18 (S31Y; N57F)
EVQLVQSGAEVKKPGASVKVSCKASGYTFTYYAMHWVRQAPGQRLEWMGWINAGNG
FTKYSQKFQGRVTITRDTSASTAYMELSSLRSEDTAVYYCARDISYGSFDYWGQGTLVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPP

SEQ ID NO. 19
TYPE: PRT
ORGANISM: ARTIFICIAL SEQUENCE
OTHER INFORMATION: HEAVY CHAIN SEQUENCE FROM A HUMAN ANTI-HUMAN FR BETA ANTIBODY
SEQ ID NO. 19 (S31Y; N57F)
MGWSWILLFLLSVTAGVHSEVQLVQSGAEVKKPGASVKVSCKASGYTFTYYAMHWVR
QAPGQRLEWMGWINAGNGFTKYSQKFQGRVTITRDTSASTAYMELSSLRSEDTAVYYC
ARDISYGSFDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK

SEQ ID NO. 20
TYPE: PRT
ORGANISM: ARTIFICIAL SEQUENCE
OTHER INFORMATION: LIGHT CHAIN SEQUENCE FROM A HUMAN ANTI-HUMAN FR BETA ANTIBODY
SEQUENCE 20 (N51F; R53L; N95I)
SSELTQDPAVSVALGQTVRITCQGDSLRSNYANWYQQKPGQAPVLVIYGQFNLPSGIPD
RFSGSSSGNTASLTITGAQAADEADYYCDSRVSTGIHVVFGGGTKLTVLG

SEQ ID NO. 21
TYPE: PRT
ORGANISM: ARTIFICIAL SEQUENCE
OTHER INFORMATION: LIGHT CHAIN SEQUENCE FROM A HUMAN ANTI-HUMAN FR BETA ANTIBODY
SEQUENCE 21 (N51F; R53L; N95I)
SSELTQDPAVSVALGQTVRITCQGDSLRSNYANWYQQKPGQAPVLVIYGQFNLPSGIPD
RFSGSSSGNTASLTITGAQAADEADYYCDSRVSTGIHVVFGGGTKLTVLGQPKAAPSVT
LFPPSSEELQANKATLVCLISDFYPGAVTVAWKADSSPVKAGVETTTPSKQSNNKYAAS
SYLSLTPEQWKSHRSYSCQVTHEGSTVEKTVAPTECS

SEQ ID NO. 22
Type: PRT
Organism: *Homo Sapiens*
SEQ ID NO. 22 (FRβ)
MVWKWMPLLLLLVCVATMCSAQDRTDLLNVCMDAKHHKTKPGPEDKLHDQCSPWK
KNACCTASTSQELHKDTSRLYNFNWDHCGKMEPACKRHFIQDTCLYECSPNLGPWIQQ
VNQSWRKERFLDVPLCKEDCQRWWEDCHTSHTCKSNWHRGWDWTSGVNKCPAGAL
CRTFESYFPTPAALCEGLWSHSYKVSNYSRGSGRCIQMWFDSAQGNPNEEVARFYAAA
MHVNAGEMLHGTGGLLLSLALMLQLWLLG SEQ ID NO. 23
Type: PRT
Other information: N-terminal amino acids from recombinantly produced FR beta
SEQ ID NO. 23
ALA ASP PRO GLY SEQ ID NO. 24 (m909 heavy)
EVQLVQSGAEVKKPGASVKVSCKASGYTFTSYAMHWVRQAPGQRLEWMGWINAGNG
NTKYSQKFQGRVTITRDTSASTAYMELSSLRSEDTAVYYCARDISYGSFDYWGQGTLVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTS SEQ ID NO. 25 (m909 light)
SSELTQDPAVSVALGQTVRITCQGDSLRSNYANWYQQKPGQAPVLVIYGQNNRPSGIPD
RFSGSSSGNTASLTITGAQAADEADYYCDSRVSTGNHVVFGGGTKLTVLGQPKAAPSVT -continued

| INFORMAL SEQUENCE LISTING |
| --- |
| LFPPSSEELQANKATLVCLISDFYPGAVTVAWKADSSPVKAGVETTTPSKQSNNKYAAS<br>SYLSLTPEQWKSHRSYSCQVTHEGSTVEKTVAPTECS |

What is claimed is:

1. An isolated human monoclonal antibody, or an antigen-binding fragment thereof, that specifically binds human folate receptor beta (FRβ), the antibody or fragment comprising: a heavy chain variable region ($V_H$) CDR 1 comprising the amino acid sequence set forth in SEQ ID NO:1; a $V_H$ CDR2 comprising the amino acid sequence set forth in SEQ ID NO:2; a $V_H$ CDR3 comprising the amino acid sequence set forth in SEQ ID NO:3; a light chain variable region ($V_L$) CDR1 comprising the amino acid sequence set forth in SEQ ID NO:4; a $V_L$ CDR2 comprising the amino acid sequence set forth in SEQ ID NO:5; and a $V_L$ CDR3 comprising the amino acid sequence set forth in SEQ ID NO:6.

2. The antibody or fragment of claim 1, wherein said antibody or fragment is de-fucosylated.

3. The antibody or fragment of claim 1, wherein the fragment is a Fab antibody fragment, a $F(ab')_2$ fragment, or a single chain antibody fragment (scFv).

4. The antibody or fragment of claim 1, wherein said antibody or fragment is conjugated with a pharmaceutical agent.

5. The antibody or fragment of claim 4, wherein said pharmaceutical agent is a chemotherapeutic.

6. The antibody or fragment of claim 1, wherein said antibody or fragment is linked to a toxin.

7. The antibody or fragment of claim 1, wherein said antibody or fragment is linked to a detectable moiety.

8. The antibody or fragment of claim 7, wherein said detectable moiety is selected from the group consisting of a fluorescent moiety, a luminescent moiety, a radioactive moiety, a CT contrast agent, an MRI contrast agent, and biotin.

9. A composition comprising the antibody or fragment of claim 1.

10. A chimeric antigen receptor comprising the antibody or fragment of claim 1.

11. An isolated human monoclonal antibody, or an antigen-binding fragment thereof, that specifically binds human folate receptor beta (FRβ), and having an equilibrium dissociation constant ($K_D$) for FRβ of 2.5 nM or less.

12. The antibody or fragment of claim 11, wherein the antibody or fragment has one or more properties selected from the group consisting of: (a) the antibody or fragment does not detectably bind to human folate receptor alpha (FRα); (b) the antibody or fragment binds to human macrophages but not to mouse macrophages; and (c) the antibody mediates antibody-dependent cellular cytotoxicity (ADCC) of FR-β expressing target cells.

13. A composition comprising the antibody or fragment of claim 11.

14. A chimeric antigen receptor comprising the antibody or fragment of claim 11.

15. A method of treating cancer in a subject, comprising administering to the subject a therapeutically effective amount of a monoclonal antibody that specifically binds human FRβ, the antibody or fragment comprising: (a) a heavy chain variable region ($V_H$) CDR 1 comprising the amino acid sequence set forth in SEQ ID NO: 1; a $V_H$ CDR2 comprising the amino acid sequence set forth in SEQ ID NO: 2; a $V_H$ CDR3 comprising the amino acid sequence set forth in SEQ ID NO: 3; a light chain variable region ($V_L$) CDR1 comprising the amino acid sequence set forth in SEQ ID NO: 4; a $V_L$ CDR2 comprising the amino acid sequence set forth in SEQ ID NO: 5; and a $V_L$ CDR3 comprising the amino acid sequence set forth in SEQ ID NO: 6.

16. The method of claim 15, wherein the antibody is a recombinant antibody, a chimeric antibody, a bispecific antibody, a humanized antibody, an IgG1 antibody, an IgG2 antibody, or an antibody fragment comprising an antigen-binding site.

17. The method of claim 15, further comprising administering at least one additional therapeutic agent.

18. The method of claim 17, wherein the additional therapeutic agent is a chemotherapeutic agent.

19. The method of claim 17, wherein the additional therapeutic agent is a second antibody.

20. The method of claim 15, wherein the cancer is selected from the group consisting of acute myeloid leukemia, colorectal cancer, ovarian cancer, pancreatic cancer, leukemia, lung cancer, liver cancer, breast cancer, kidney cancer, prostate cancer, gastrointestinal cancer, melanoma, cervical cancer, bladder cancer, glioblastoma, and head and neck cancer.

* * * * *

SEQUENCE LISTING

```
<160> NUMBER OF SEQ ID NOS: 25

<210> SEQ ID NO 1
<211> LENGTH: 8
<212> TYPE: PRT
<213> ORGANISM: Artificial Sequence
<220> FEATURE:
<223> OTHER INFORMATION: HEAVY CHAIN COMPLEMENTARY DETERMINING REGION
      FROM A HUMAN ANTI-HUMAN FR BETA ANTIBODY

<400> SEQUENCE: 1

Gly Tyr Thr Phe Thr Tyr Tyr Ala
1               5


<210> SEQ ID NO 2
<211> LENGTH: 7
<212> TYPE: PRT
<213> ORGANISM: Artificial Sequence
<220> FEATURE:
<223> OTHER INFORMATION: HEAVY CHAIN COMPLEMENTARY DETERMINING REGION
      FROM A HUMAN ANTI-HUMAN FR BETA ANTIBODY

<400> SEQUENCE: 2

Lys Tyr Ser Gln Lys Phe Gln
1               5


<210> SEQ ID NO 3
<211> LENGTH: 12
<212> TYPE: PRT
<213> ORGANISM: Artificial Sequence
<220> FEATURE:
<223> OTHER INFORMATION: HEAVY CHAIN COMPLEMENTARY DETERMINING REGION
      FROM A HUMAN ANTI-HUMAN FR BETA ANTIBODY

<400> SEQUENCE: 3

Ala Arg Asp Ile Ser Tyr Gly Ser Phe Asp Tyr Trp
1               5                   10


<210> SEQ ID NO 4
<211> LENGTH: 6
<212> TYPE: PRT
<213> ORGANISM: Artificial Sequence
<220> FEATURE:
<223> OTHER INFORMATION: LIGHT CHAIN COMPLEMENTARY DETERMINING REGION
      FROM A HUMAN ANTI-HUMAN FR BETA ANTIBODY

<400> SEQUENCE: 4

Ser Leu Arg Ser Asn Tyr
1               5


<210> SEQ ID NO 5
<211> LENGTH: 3
<212> TYPE: PRT
<213> ORGANISM: Artificial Sequence
<220> FEATURE:
<223> OTHER INFORMATION: LIGHT CHAIN COMPLEMENTARY DETERMINING REGION
      FROM A HUMAN ANTI-HUMAN FR BETA ANTIBODY

<400> SEQUENCE: 5
```

```
Gly Gln Phe
1


<210> SEQ ID NO 6
<211> LENGTH: 12
<212> TYPE: PRT
<213> ORGANISM: Artificial Sequence
<220> FEATURE:
<223> OTHER INFORMATION: LIGHT CHAIN COMPLEMENTARY DETERMINING REGION
      FROM A HUMAN ANTI-HUMAN FR BETA ANTIBODY

<400> SEQUENCE: 6

Asp Ser Arg Val Ser Thr Gly Ile His Val Val Phe
1               5                   10


<210> SEQ ID NO 7
<211> LENGTH: 118
<212> TYPE: PRT
<213> ORGANISM: Artificial Sequence
<220> FEATURE:
<223> OTHER INFORMATION: HEAVY CHAIN SEQUENCE FROM A HUMAN ANTI-HUMAN FR
      BETA ANTIBODY

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Ser Tyr Gly Ser Phe Asp Tyr Trp Gly Gln Gly Thr
            100                 105                 110

Leu Val Thr Val Ser Ser
        115


<210> SEQ ID NO 8
<211> LENGTH: 229
<212> TYPE: PRT
<213> ORGANISM: Artificial Sequence
<220> FEATURE:
<223> OTHER INFORMATION: HEAVY CHAIN SEQUENCE FROM A HUMAN ANTI-HUMAN FR
      BETA ANTIBODY

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
```

```
                85                  90                  95

Ala Arg Asp Ile Ser Tyr Gly Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro
225


<210> SEQ ID NO 9
<211> LENGTH: 467
<212> TYPE: PRT
<213> ORGANISM: Artificial Sequence
<220> FEATURE:
<223> OTHER INFORMATION: HEAVY CHAIN SEQUENCE FROM A HUMAN ANTI-HUMAN FR
      BETA ANTIBODY

<400> SEQUENCE: 9

Met Gly Trp Ser Trp Ile Leu Leu Phe Leu Leu Ser Val Thr Ala Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Tyr Tyr Ala Met His Trp Val Arg Gln Ala Pro Gly Gln Arg Leu
    50                  55                  60

Glu Trp Met Gly Trp Ile Asn Ala Gly Asn Gly Asn Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ile Ser Tyr Gly Ser Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205
```

```
Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 10
<211> LENGTH: 1404
<212> TYPE: DNA
<213> ORGANISM: Artificial Sequence
<220> FEATURE:
<223> OTHER INFORMATION: NUCLEIC ACID SEQUENCE ENCODING HEAVY CHAIN FROM
      A HUMAN ANTI-HUMAN FR BETA ANTIBODY

<400> SEQUENCE: 10

atgggctgga gctggatcct gctgttcctc ctgagcgtga cagcaggagt gcacagcgag     60

gtgcagctgg tccagtccgg cgctgaggtg aagaaaccag gggcatccgt gaaagtctcc    120

tgcaaagcca gtggctacac cttcacatac tatgccatgc actgggtgag gcaggctcca    180

ggacagcgac tggaatggat gggctggatc aacgccggca acgggaatac taagtactcc    240

cagaaatttc aggggcgggt gactattacc agagacacct cagccagcac agcttatatg    300

gagctgagct ccctgcgaag cgaagataca gcagtctact attgtgccag agacattagt    360

tacggaagct ttgattattg gggacagggc acactggtga ctgtctctag tgctagcacc    420

aagggcccat cggtcttccc cctggcaccc tcctccaaga gcacctctgg gggcacagcg    480

gccctgggct gcctggtcaa ggactacttc cccgaaccgg tgacggtgtc gtggaactca    540
```

```
ggcgccctga ccagcggcgt gcacaccttc ccggctgtcc tacagtcctc aggactctac    600

tccctcagca gcgtggtgac cgtgccctcc agcagcttgg gcacccagac ctacatctgc    660

aacgtgaatc acaagcccag caacaccaag gtggacaaga aagttgagcc caaatcttgt    720

gacaaaactc acacatgccc accgtgccca gcacctgaac tcctgggggg accgtcagtc    780

ttcctcttcc ccccaaaacc caaggacacc ctcatgatct cccggacccc tgaggtcaca    840

tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggatga gctgaccaag   1140

aaccaggtca gcctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcta cagcaagctc accgtggaca agagcaggtg gcagcagggg   1320

aacgtcttct catgctccgt gatgcatgag gctctgcaca accactacac gcagaagagc   1380

ctctccctgt ctccgggtaa atga                                          1404
```

```
<210> SEQ ID NO 11
<211> LENGTH: 109
<212> TYPE: PRT
<213> ORGANISM: Artificial Sequence
<220> FEATURE:
<223> OTHER INFORMATION: LIGHT CHAIN SEQUENCE FROM A HUMAN ANTI-HUMAN FR
      BETA ANTIBODY

<400> SEQUENCE: 11

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Asn Tyr Ala
            20                  25                  30

Asn Trp Tyr Gln Gln Lys Pro Gly Gln Ala Pro Val Leu Val Ile Tyr
        35                  40                  45

Gly Gln Phe Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Ala
65                  70                  75                  80

Asp Glu Ala Asp Tyr Tyr Cys Asp Ser Arg Val Ser Thr Gly Ile His
                85                  90                  95

Val Val Phe Gly Gly Gly Thr Lys Leu Thr Val Leu Gly
            100                 105


<210> SEQ ID NO 12
<211> LENGTH: 214
<212> TYPE: PRT
<213> ORGANISM: Artificial Sequence
<220> FEATURE:
<223> OTHER INFORMATION: LIGHT CHAIN SEQUENCE FROM A HUMAN ANTI-HUMAN FR
      BETA ANTIBODY

<400> SEQUENCE: 12

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Asn Tyr Ala
            20                  25                  30
```

```
Asn Trp Tyr Gln Gln Lys Pro Gly Gln Ala Pro Val Leu Val Ile Tyr
        35                  40                  45

Gly Gln Phe Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Ala
65                  70                  75                  80

Asp Glu Ala Asp Tyr Tyr Cys Asp Ser Arg Val Ser Thr Gly Ile His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 13
<211> LENGTH: 702
<212> TYPE: DNA
<213> ORGANISM: Artificial Sequence
<220> FEATURE:
<223> OTHER INFORMATION: NUCLEIC ACID SEQUENCE ENCODING LIGHT CHAIN FROM
      A HUMAN ANTI-HUMAN FR BETA ANTIBODY

<400> SEQUENCE: 13

atgggctgga gctggatcct gctgttcctc ctgagcgtga cagcaggagt gcacagctct      60

tctgaactta ctcaagatcc cgccgtgtcc gtggccctgg gccagaccgt gaggatcacc     120

tgccagggcg actccctgag gtccaactac gccaattggt accagcagaa gcccggccag     180

gcccccgtgc tggtcatcta cggccagttc aacaggccct ccggcatccc cgaccgcttc     240

tccggctcct cctccggcaa caccgcctcc ctgaccatca ccggcgccca ggccgcagac     300

gaggccgact actactgcga ttccagggtg tccaccggca tccacgtggt gttcggcggc     360

ggcaccaagc tgaccgtgct gggccagccc aaggccgccc cctccgtgac cctgttcccc     420

ccctcctccg aggagctgca ggccaacaag gccaccctgg tctgcctgat ctccgacttc     480

taccccggcg ccgtgaccgt ggcctggaag gccgactcct cccccgtgaa ggccggcgtg     540

gagacaacca ccccctccaa gcagtccaac aacaaatacg ccgcctcctc ctacctgtcc     600

ctgacccccg agcagtggaa gtcccacagg tcctactcct gccaagtcac ccacgagggc     660

tccaccgtgg agaagaccgt ggcccccacc gagtgctcct ag                        702


<210> SEQ ID NO 14
<211> LENGTH: 3
<212> TYPE: PRT
<213> ORGANISM: Artificial Sequence
<220> FEATURE:
<223> OTHER INFORMATION: LIGHT CHAIN COMPLEMENTARY DETERMINING REGION
```

FROM A HUMAN ANTI-HUMAN FR BETA ANTIBODY

<400> SEQUENCE: 14

```
Gly Gln Asn
1
```

<210> SEQ ID NO 15
<211> LENGTH: 109
<212> TYPE: PRT
<213> ORGANISM: Artificial Sequence
<220> FEATURE:
<223> OTHER INFORMATION: LIGHT CHAIN SEQUENCE FROM A HUMAN ANTI-HUMAN FR BETA ANTIBODY

<400> SEQUENCE: 15

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Asn Tyr Ala
            20                  25                  30

Asn Trp Tyr Gln Gln Lys Pro Gly Gln Ala Pro Val Leu Val Ile Tyr
        35                  40                  45

Gly Gln Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Ala
65                  70                  75                  80

Asp Glu Ala Asp Tyr Tyr Cys Asp Ser Arg Val Ser Thr Gly Ile His
                85                  90                  95

Val Val Phe Gly Gly Gly Thr Lys Leu Thr Val Leu Gly
            100                 105
```

<210> SEQ ID NO 16
<211> LENGTH: 214
<212> TYPE: PRT
<213> ORGANISM: Artificial Sequence
<220> FEATURE:
<223> OTHER INFORMATION: LIGHT CHAIN SEQUENCE FROM A HUMAN ANTI-HUMAN FR BETA ANTIBODY

<400> SEQUENCE: 16

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Asn Tyr Ala
            20                  25                  30

Asn Trp Tyr Gln Gln Lys Pro Gly Gln Ala Pro Val Leu Val Ile Tyr
        35                  40                  45

Gly Gln Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Ala
65                  70                  75                  80

Asp Glu Ala Asp Tyr Tyr Cys Asp Ser Arg Val Ser Thr Gly Ile His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160
```

```
Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 17
<211> LENGTH: 118
<212> TYPE: PRT
<213> ORGANISM: Artificial Sequence
<220> FEATURE:
<223> OTHER INFORMATION: HEAVY CHAIN SEQUENCE FROM A HUMAN ANTI-HUMAN FR BETA ANTIBODY

<400> SEQUENCE: 17

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Phe Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Ser Tyr Gly Ser Phe Asp Tyr Trp Gly Gln Gly Thr
            100                 105                 110

Leu Val Thr Val Ser Ser
        115
```

<210> SEQ ID NO 18
<211> LENGTH: 229
<212> TYPE: PRT
<213> ORGANISM: Artificial Sequence
<220> FEATURE:
<223> OTHER INFORMATION: HEAVY CHAIN SEQUENCE FROM A HUMAN ANTI-HUMAN FR BETA ANTIBODY

<400> SEQUENCE: 18

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Phe Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Ser Tyr Gly Ser Phe Asp Tyr Trp Gly Gln Gly Thr
            100                 105                 110
```

```
Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro
225


<210> SEQ ID NO 19
<211> LENGTH: 467
<212> TYPE: PRT
<213> ORGANISM: Artificial Sequence
<220> FEATURE:
<223> OTHER INFORMATION: HEAVY CHAIN SEQUENCE FROM A HUMAN ANTI-HUMAN FR
      BETA ANTIBODY

<400> SEQUENCE: 19

Met Gly Trp Ser Trp Ile Leu Leu Phe Leu Leu Ser Val Thr Ala Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Tyr Tyr Ala Met His Trp Val Arg Gln Ala Pro Gly Gln Arg Leu
    50                  55                  60

Glu Trp Met Gly Trp Ile Asn Ala Gly Asn Gly Phe Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Ile Ser Tyr Gly Ser Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
```

```
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 20
<211> LENGTH: 109
<212> TYPE: PRT
<213> ORGANISM: Artificial Sequence
<220> FEATURE:
<223> OTHER INFORMATION: LIGHT CHAIN SEQUENCE FROM A HUMAN ANTI-HUMAN FR
      BETA ANTIBODY

<400> SEQUENCE: 20

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Asn Tyr Ala
            20                  25                  30

Asn Trp Tyr Gln Gln Lys Pro Gly Gln Ala Pro Val Leu Val Ile Tyr
        35                  40                  45

Gly Gln Phe Asn Leu Pro Ser Gly Ile Pro Asp Arg Phe Ser Gly Ser
    50                  55                  60

Ser Ser Gly Asn Thr Ala Ser Leu Thr Ile Thr Gly Ala Gln Ala Ala
65                  70                  75                  80

Asp Glu Ala Asp Tyr Tyr Cys Asp Ser Arg Val Ser Thr Gly Ile His
                85                  90                  95

Val Val Phe Gly Gly Gly Thr Lys Leu Thr Val Leu Gly
            100                 105
```

<210> SEQ ID NO 21
<211> LENGTH: 214
<212> TYPE: PRT
<213> ORGANISM: Artificial Sequence
<220> FEATURE:
<223> OTHER INFORMATION: LIGHT CHAIN SEQUENCE FROM A HUMAN ANTI-HUMAN FR BETA ANTIBODY

<400> SEQUENCE: 21

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Asn Tyr Ala
            20                  25                  30

Asn Trp Tyr Gln Gln Lys Pro Gly Gln Ala Pro Val Leu Val Ile Tyr
        35                  40                  45

Gly Gln Phe Asn Leu Pro Ser Gly Ile Pro Asp Arg Phe Ser Gly Ser
    50                  55                  60

Ser Ser Gly Asn Thr Ala Ser Leu Thr Ile Thr Gly Ala Gln Ala Ala
65                  70                  75                  80

Asp Glu Ala Asp Tyr Tyr Cys Asp Ser Arg Val Ser Thr Gly Ile His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 22
<211> LENGTH: 255
<212> TYPE: PRT
<213> ORGANISM: Homo sapiens

<400> SEQUENCE: 22

```
Met Val Trp Lys Trp Met Pro Leu Leu Leu Leu Leu Val Cys Val Ala
1               5                   10                  15

Thr Met Cys Ser Ala Gln Asp Arg Thr Asp Leu Leu Asn Val Cys Met
            20                  25                  30

Asp Ala Lys His His Lys Thr Lys Pro Gly Pro Glu Asp Lys Leu His
        35                  40                  45

Asp Gln Cys Ser Pro Trp Lys Lys Asn Ala Cys Cys Thr Ala Ser Thr
    50                  55                  60

Ser Gln Glu Leu His Lys Asp Thr Ser Arg Leu Tyr Asn Phe Asn Trp
65                  70                  75                  80

Asp His Cys Gly Lys Met Glu Pro Ala Cys Lys Arg His Phe Ile Gln
                85                  90                  95
```

-continued

```
Asp Thr Cys Leu Tyr Glu Cys Ser Pro Asn Leu Gly Pro Trp Ile Gln
            100                 105                 110

Gln Val Asn Gln Ser Trp Arg Lys Glu Arg Phe Leu Asp Val Pro Leu
        115                 120                 125

Cys Lys Glu Asp Cys Gln Arg Trp Trp Glu Asp Cys His Thr Ser His
    130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255


<210> SEQ ID NO 23
<211> LENGTH: 4
<212> TYPE: PRT
<213> ORGANISM: Artificial Sequence
<220> FEATURE:
<223> OTHER INFORMATION: N-terminal amino acids from recombinantly
      produced FR beta

<400> SEQUENCE: 23

Ala Asp Pro Gly
1


<210> SEQ ID NO 24
<211> LENGTH: 225
<212> TYPE: PRT
<213> ORGANISM: Artificial Sequence
<220> FEATURE:
<223> OTHER INFORMATION: Heavy chain amino acid seqeunce for antibody
      binding FR-Beta

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Ser Tyr Gly Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

Ser
225


<210> SEQ ID NO 25
<211> LENGTH: 214
<212> TYPE: PRT
<213> ORGANISM: Artificial Sequence
<220> FEATURE:
<223> OTHER INFORMATION: Light chain amino acid sequence for antibody
      binding FR-Beta

<400> SEQUENCE: 25

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Asn Tyr Ala
            20                  25                  30

Asn Trp Tyr Gln Gln Lys Pro Gly Gln Ala Pro Val Leu Val Ile Tyr
        35                  40                  45

Gly Gln Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Ala
65                  70                  75                  80

Asp Glu Ala Asp Tyr Tyr Cys Asp Ser Arg Val Ser Thr Gly Asn His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```